United States Patent
Iorio et al.

(10) Patent No.: US 11,878,172 B2
(45) Date of Patent: Jan. 23, 2024

(54) SYSTEM AND METHOD FOR QUANTIFYING QUALITATIVE PATIENT-REPORTED DATA SETS

(71) Applicant: Neuros Medical, Inc., Aliso Viejo, CA (US)

(72) Inventors: Matthew John Iorio, University Heights, OH (US); Nemath Syed Shah, Lyndhurst, OH (US)

(73) Assignee: Neuros Medical, Inc., Aliso Viejo, CA (US)

( * ) Notice: Subject to any disclaimer, the term of this patent is extended or adjusted under 35 U.S.C. 154(b) by 300 days.

(21) Appl. No.: 17/174,014

(22) Filed: Feb. 11, 2021

(65) Prior Publication Data
US 2021/0244952 A1 Aug. 12, 2021

Related U.S. Application Data

(60) Provisional application No. 62/975,093, filed on Feb. 11, 2020.

(51) Int. Cl.
*A61N 1/36* (2006.01)

(52) U.S. Cl.
CPC ..... *A61N 1/36132* (2013.01); *A61N 1/36071* (2013.01)

(58) Field of Classification Search
CPC .......... A61N 1/36132; A61N 1/36071
See application file for complete search history.

(56) References Cited

U.S. PATENT DOCUMENTS

| 3,738,368 A | 6/1973 | Avery et al. |
| 4,155,366 A | 5/1979 | Di Mucci |
(Continued)

FOREIGN PATENT DOCUMENTS

| CN | 102573986 A | 7/2012 |
| DE | 202010015346 U1 | 4/2011 |
(Continued)

OTHER PUBLICATIONS

Ackermann et al.; Effect of bipolar cuff electrode design on block thresholds in high-frequency electrical neural conduction block; IEEE Transactions on Neural Systems and Rehabilitation Engineering; 17(5); pp. 469-477; Oct. 1, 2009.
(Continued)

*Primary Examiner* — Alyssa M Alter
(74) *Attorney, Agent, or Firm* — Shay Glenn LLP

(57) ABSTRACT

Methods and apparatuses for collecting and quantifying patient-reported data from a neuromodulator. The patient-reported data typically includes a pain score that quantifies the level of pain experienced by the patient at a particular time. The apparatus can include a user interface that allows the patient to enter such information in real time. The methods and apparatuses can include a correlation process, whereby each patient-reported entry is correlated with a corresponding neuromodulation treatment. This correlation can be used to identify treatment parameters and dosages that are most effective, and to further identify when certain dosages are most effective. This information can further be used as feedback to generate optimized treatments for a specific patient and iteratively improve the treatments. In some cases, the correlation process identifies under reported or over reported data, which can be filtered out to provide more accurate optimized treatments.

31 Claims, 11 Drawing Sheets

(56) References Cited

U.S. PATENT DOCUMENTS

| | | |
|---|---|---|
| 4,573,481 A | 3/1986 | Bullara |
| 4,602,624 A | 7/1986 | Naples et al. |
| 4,979,511 A | 12/1990 | Terry |
| 5,143,067 A | 9/1992 | Rise et al. |
| 5,324,322 A | 6/1994 | Grill et al. |
| 5,653,739 A | 8/1997 | Maurer et al. |
| 5,755,750 A | 5/1998 | Petruska et al. |
| 5,964,702 A | 10/1999 | Grill, Jr. et al. |
| 6,058,331 A | 5/2000 | King |
| 6,275,735 B1 | 8/2001 | Jarding et al. |
| 6,292,703 B1 | 9/2001 | Meier et al. |
| 6,456,866 B1 | 9/2002 | Tyler et al. |
| 6,699,275 B1 | 3/2004 | Knudson et al. |
| 6,735,475 B1 | 5/2004 | Whitehurst et al. |
| 6,760,626 B1 | 7/2004 | Boveja |
| 6,836,685 B1 | 12/2004 | Fitz |
| 6,860,851 B2 | 3/2005 | Knudson et al. |
| 6,871,099 B1 | 3/2005 | Whitehurst et al. |
| 7,076,307 B2 | 7/2006 | Boveja et al. |
| 7,167,750 B2 | 1/2007 | Knudson et al. |
| 7,201,757 B2 | 4/2007 | Knudson et al. |
| 7,292,890 B2 | 11/2007 | Whitehurst et al. |
| 7,295,876 B1 | 11/2007 | Erickson |
| 7,302,296 B1 | 11/2007 | Hoffer |
| 7,324,852 B2 | 1/2008 | Barolat et al. |
| 7,389,145 B2 | 6/2008 | Kilgore et al. |
| 7,444,183 B2 | 10/2008 | Knudson et al. |
| 7,463,927 B1 | 12/2008 | Chaouat |
| 7,489,966 B2 | 2/2009 | Leinders et al. |
| 7,555,345 B2 | 6/2009 | Wahlstrand et al. |
| 7,616,990 B2 | 11/2009 | Chavan et al. |
| 7,761,166 B2 | 7/2010 | Giftakis et al. |
| 7,839,415 B2 | 11/2010 | Hillard et al. |
| 7,860,570 B2 | 12/2010 | Whitehurst et al. |
| 7,894,905 B2 | 2/2011 | Pless et al. |
| 7,894,906 B2 | 2/2011 | Shuros |
| 7,979,131 B2 | 7/2011 | Feler et al. |
| 8,027,718 B2 | 9/2011 | Spinner et al. |
| 8,060,208 B2 | 11/2011 | Kilgore et al. |
| 8,060,209 B2 | 11/2011 | Jaax et al. |
| 8,108,052 B2 | 1/2012 | Boling |
| 8,116,882 B2 | 2/2012 | Kowalczewski |
| 8,170,675 B2 | 5/2012 | Alataris et al. |
| 8,185,207 B2 | 5/2012 | Molnar et al. |
| 8,219,202 B2 | 7/2012 | Giftakis et al. |
| 8,224,453 B2 | 7/2012 | De Ridder |
| 8,380,318 B2 | 2/2013 | Kishawi et al. |
| 8,452,417 B2 | 5/2013 | Navarro |
| 8,467,879 B1 | 6/2013 | Whitehurst et al. |
| 8,498,711 B2 | 7/2013 | Roche |
| 8,504,147 B2 | 8/2013 | Deem et al. |
| 8,521,291 B1 | 8/2013 | Cholette et al. |
| 8,560,075 B2 | 10/2013 | Covalin |
| 8,594,796 B2 | 11/2013 | Roche |
| 8,600,505 B2 | 12/2013 | Libbus et al. |
| 8,676,329 B2 | 3/2014 | Wacnik et al. |
| 8,676,331 B2 | 3/2014 | Parker |
| 8,712,547 B2 | 4/2014 | Whitehurst et al. |
| 8,731,676 B2 | 5/2014 | Fang et al. |
| 8,738,140 B2 | 5/2014 | De Ridder |
| 8,755,893 B2 | 6/2014 | Gross et al. |
| 8,761,892 B2 | 6/2014 | Weisgarber et al. |
| 8,788,045 B2 | 7/2014 | Gross et al. |
| 8,805,518 B2 | 8/2014 | King et al. |
| 8,903,502 B2 | 12/2014 | Perryman et al. |
| 8,923,975 B2 | 12/2014 | Bradley |
| 8,965,516 B2 | 2/2015 | Bennett et al. |
| 8,977,362 B2 | 3/2015 | Saab |
| 8,983,612 B2 | 3/2015 | Fang et al. |
| 8,983,614 B2 | 3/2015 | Kilgore et al. |
| 9,031,658 B2 | 5/2015 | Chiao et al. |
| 9,037,248 B2 | 5/2015 | Durand et al. |
| 9,089,700 B2 | 7/2015 | Hlavka et al. |
| 9,095,699 B2 | 8/2015 | Rosenberg et al. |
| 9,132,272 B2 | 9/2015 | Alves et al. |
| 9,259,575 B2 | 2/2016 | Zhao et al. |
| 9,295,840 B1 | 3/2016 | Thacker et al. |
| 9,295,841 B2 | 3/2016 | Fang et al. |
| 9,327,121 B2 | 5/2016 | Thacker et al. |
| 9,339,655 B2 | 5/2016 | Carbunaru |
| 9,387,325 B1 | 7/2016 | Min et al. |
| 9,403,008 B2 | 8/2016 | Howard |
| 9,403,014 B2 | 8/2016 | Kilgore et al. |
| 9,409,019 B2 | 8/2016 | Walker et al. |
| 9,421,372 B2 | 8/2016 | Mashiach et al. |
| 9,604,062 B2 | 3/2017 | Carroll |
| 9,630,011 B2 | 4/2017 | Lipani |
| 9,694,181 B2 | 7/2017 | Bhadra et al. |
| 9,814,881 B2 | 11/2017 | Moffitt |
| 9,884,189 B2 | 2/2018 | Boggs |
| 9,884,192 B2 | 2/2018 | Kilgore et al. |
| 9,889,293 B2 | 2/2018 | Siegel et al. |
| 9,931,510 B2 | 4/2018 | Hou et al. |
| 9,937,348 B1 | 4/2018 | Bradley |
| 9,956,398 B2 | 5/2018 | Callegari et al. |
| 10,086,201 B2 | 10/2018 | Chang et al. |
| 10,105,541 B2 | 10/2018 | Kishawi et al. |
| 10,149,978 B1 | 12/2018 | Park |
| 10,159,838 B2 | 12/2018 | Kim et al. |
| 10,195,434 B2 | 2/2019 | Bhadra et al. |
| 10,238,872 B2 | 3/2019 | Pivonka et al. |
| 10,258,805 B2 | 4/2019 | Reed et al. |
| 10,286,213 B2 | 5/2019 | Fletcher et al. |
| 10,300,273 B2 | 5/2019 | Rooney et al. |
| 10,315,034 B2 | 6/2019 | Hou et al. |
| 10,328,256 B1 | 6/2019 | Gliner |
| 10,390,877 B2 | 8/2019 | Heggeness et al. |
| 10,456,575 B2 | 10/2019 | Kilgore et al. |
| 10,617,870 B2 | 4/2020 | Kilgore et al. |
| 10,632,309 B2 | 4/2020 | McGee et al. |
| 10,675,469 B2 | 6/2020 | Annoni et al. |
| 10,722,703 B2 | 7/2020 | Mitchell |
| 10,758,723 B2 | 9/2020 | Fang et al. |
| 10,780,270 B2 | 9/2020 | Schepis et al. |
| 10,786,669 B2 | 9/2020 | Rajguru et al. |
| 10,799,701 B2 | 10/2020 | Lee |
| 10,828,491 B2 | 11/2020 | Schepis et al. |
| 10,864,373 B2 | 12/2020 | Bhadra et al. |
| 10,894,159 B2 | 1/2021 | De Ridder |
| 10,926,092 B2 | 2/2021 | Esteller et al. |
| 10,953,228 B2 | 3/2021 | Perryman et al. |
| 10,967,183 B2 | 4/2021 | Yakovlev et al. |
| 11,007,364 B2 | 5/2021 | Carroll |
| 11,027,126 B2 | 6/2021 | Ackermann et al. |
| 11,071,863 B2 | 7/2021 | Torgerson |
| 11,116,975 B2 | 9/2021 | Oron et al. |
| 11,167,129 B2 | 11/2021 | Parker |
| 11,235,146 B2 | 2/2022 | Boggs et al. |
| 11,247,053 B2 | 2/2022 | Rajguru et al. |
| 11,253,705 B1 | 2/2022 | John |
| 11,278,718 B2 | 3/2022 | Faltys et al. |
| 11,311,726 B2 | 4/2022 | Vansickle et al. |
| 11,331,489 B2 | 5/2022 | Johanek |
| 11,331,493 B2 | 5/2022 | Pivonka et al. |
| 11,344,726 B2 | 5/2022 | Bennett et al. |
| 11,344,729 B1 | 5/2022 | Single et al. |
| 2002/0055779 A1 | 5/2002 | Andrews |
| 2002/0198572 A1 | 12/2002 | Weiner |
| 2003/0144709 A1 | 7/2003 | Zabara et al. |
| 2004/0015205 A1 | 1/2004 | Whitehurst et al. |
| 2004/0111139 A1 | 6/2004 | McCreery |
| 2004/0147977 A1 | 7/2004 | Petrofsky |
| 2004/0243182 A1 | 12/2004 | Cohen et al. |
| 2005/0131485 A1 | 6/2005 | Knudson et al. |
| 2005/0137648 A1 | 6/2005 | Cosendai et al. |
| 2005/0143789 A1 | 6/2005 | Whitehurst et al. |
| 2005/0149148 A1 | 7/2005 | King |
| 2005/0149154 A1 | 7/2005 | Cohen et al. |
| 2006/0025832 A1 | 2/2006 | O'Keeffe et al. |
| 2006/0030919 A1 | 2/2006 | Mrva et al. |
| 2006/0184211 A1 | 8/2006 | Gaunt et al. |
| 2006/0195158 A1 | 8/2006 | Cory |
| 2006/0270944 A1 | 11/2006 | King et al. |
| 2006/0271137 A1 | 11/2006 | Stanton-Hicks |

(56) References Cited

U.S. PATENT DOCUMENTS

| | | |
|---|---|---|
| 2006/0293721 A1 | 12/2006 | Tarver et al. |
| 2007/0043400 A1 | 2/2007 | Donders |
| 2007/0142863 A1 | 6/2007 | Bradley |
| 2007/0185549 A1 | 8/2007 | Zdeblick |
| 2008/0027505 A1 | 1/2008 | Levin et al. |
| 2008/0046055 A1 | 2/2008 | Durand et al. |
| 2008/0086180 A1 | 4/2008 | Ben-Ezra et al. |
| 2008/0172116 A1 | 7/2008 | Mrva et al. |
| 2008/0183226 A1 | 7/2008 | Buras et al. |
| 2008/0228194 A1 | 9/2008 | Westlund et al. |
| 2008/0319511 A1 | 12/2008 | Pless |
| 2009/0069738 A1 | 3/2009 | Rossing et al. |
| 2009/0083070 A1 | 3/2009 | Giftakis et al. |
| 2009/0204173 A1 | 8/2009 | Fang et al. |
| 2009/0281595 A1 | 11/2009 | King et al. |
| 2010/0121408 A1 | 5/2010 | Imran et al. |
| 2010/0152808 A1 | 6/2010 | Boggs, II |
| 2010/0168820 A1 | 7/2010 | Maniak et al. |
| 2010/0211135 A1 | 8/2010 | Caparso et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0071593 A1 | 3/2011 | Parker et al. |
| 2011/0230701 A1 | 9/2011 | Simon et al. |
| 2012/0016439 A1 | 1/2012 | Alataris et al. |
| 2012/0083709 A1 | 4/2012 | Parker et al. |
| 2012/0083856 A1 | 4/2012 | Thacker et al. |
| 2012/0089199 A1 | 4/2012 | Bolea et al. |
| 2012/0232615 A1 | 9/2012 | Barolat et al. |
| 2012/0253261 A1 | 10/2012 | Poletto et al. |
| 2013/0035735 A1 | 2/2013 | Kroll |
| 2013/0289664 A1 | 10/2013 | Johanek |
| 2013/0289667 A1 | 10/2013 | Wacnik et al. |
| 2014/0046398 A1 | 2/2014 | Sachs et al. |
| 2014/0188186 A1 | 7/2014 | Barolat et al. |
| 2014/0228905 A1 | 8/2014 | Bolea |
| 2015/0230809 A1 | 8/2015 | Becker |
| 2016/0256685 A1 | 9/2016 | Haessler |
| 2016/0361542 A1 | 12/2016 | Kaula et al. |
| 2017/0007836 A1 | 1/2017 | Nassif |
| 2017/0095667 A1 | 4/2017 | Yakovlev et al. |
| 2017/0239486 A1 | 8/2017 | Suryavanshi |
| 2017/0319381 A1 | 11/2017 | Rogers |
| 2017/0333701 A1 | 11/2017 | Bradley et al. |
| 2017/0348532 A1 | 12/2017 | Moffitt et al. |
| 2018/0008827 A1 | 1/2018 | Dolev et al. |
| 2018/0021577 A1 | 1/2018 | Phillips |
| 2018/0043172 A1 | 2/2018 | Serrano Carmona |
| 2018/0056066 A1 | 3/2018 | Boggs et al. |
| 2018/0140835 A1* | 5/2018 | Sharma .................. G16H 10/60 |
| 2018/0333576 A1 | 11/2018 | Rigaux |
| 2019/0151659 A1 | 5/2019 | Mishra et al. |
| 2019/0184170 A1 | 6/2019 | Knudson et al. |
| 2019/0308020 A1 | 10/2019 | Syed Shah et al. |
| 2019/0358455 A1 | 11/2019 | Lin et al. |
| 2019/0358466 A1 | 11/2019 | Leung et al. |
| 2019/0374779 A1 | 12/2019 | Kilgore et al. |
| 2020/0324113 A1 | 10/2020 | Fisher et al. |
| 2020/0368518 A1 | 11/2020 | Vera-Portocarrero et al. |
| 2020/0391032 A1 | 12/2020 | Fang et al. |
| 2021/0008366 A1 | 1/2021 | Snyder |
| 2021/0069501 A1 | 3/2021 | Molnar et al. |
| 2021/0113840 A1 | 4/2021 | Bhadra et al. |
| 2021/0154478 A1 | 5/2021 | Hincapie Ordonez et al. |
| 2021/0236820 A1 | 8/2021 | Parker et al. |
| 2021/0252288 A1 | 8/2021 | Lin et al. |
| 2021/0260381 A1 | 8/2021 | Kilgore et al. |
| 2021/0283398 A1 | 9/2021 | Kibler et al. |
| 2021/0283401 A1 | 9/2021 | Tai |
| 2021/0308456 A1 | 10/2021 | Gliner et al. |
| 2022/0008723 A1 | 1/2022 | Hsu et al. |
| 2022/0016421 A1 | 1/2022 | Boggs et al. |
| 2022/0023634 A1 | 1/2022 | Parker et al. |
| 2022/0023635 A1 | 1/2022 | Pepin et al. |
| 2022/0023648 A1 | 1/2022 | Doan et al. |
| 2022/0032060 A1 | 2/2022 | Bhadra et al. |
| 2022/0072315 A1 | 3/2022 | Zhang et al. |
| 2022/0152393 A1 | 5/2022 | Kent et al. |
| 2022/0176108 A1 | 6/2022 | Linden et al. |
| 2022/0339446 A1 | 10/2022 | Fang et al. |

FOREIGN PATENT DOCUMENTS

| | | |
|---|---|---|
| EP | 3219357 A1 | 9/2017 |
| JP | 2009522015 A | 6/2009 |
| JP | 2012130579 A | 7/2012 |
| WO | WO00/61222 A1 | 10/2000 |
| WO | WO2005/105202 A1 | 11/2005 |
| WO | WO2007/117347 A1 | 10/2007 |
| WO | WO2009/079270 A1 | 6/2009 |
| WO | WO2012/159002 A8 | 11/2012 |
| WO | WO2018/033855 A1 | 2/2018 |
| WO | WO2018/067239 A1 | 4/2018 |
| WO | WO2018/106839 A2 | 6/2018 |
| WO | WO2020/041323 A1 | 2/2020 |
| WO | WO2020/243096 A1 | 12/2020 |
| WO | WO2021/003151 A1 | 1/2021 |
| WO | WO2021/111371 A1 | 6/2021 |
| WO | WO2021/216568 A1 | 10/2021 |

OTHER PUBLICATIONS

Ackermann et al.; Electrical conduction block in large nerves: high frequency current delivery in the nonhuman primate; Muscle and Nerve. 43(6); pp. 897-899; Jun. 2011.

Becker et al.; Essentials of local anesthetic pharmacology; Anesthesia progress; 53(3); pp. 98-109; Sep. 2006.

Bhadra et al.; High-frequency electrical conduction block of mammalian peripheral motor nerve; Muscle and Nerve; 32(6); pp. 782-790; Dec. 2005.

Bhadra et al.; Simulation of high-frequency sinusoidal electrical block of mammalian myelinated axons; Journal of Computational Neuroscience; 22(3); pp. 313-326; Jun. 1, 2007.

Bouaziz et al.; Neurologic complication of peripheral neural blockade. In Cousins and Bridenbaugh's Neural blockade in clinical anesthesia and pain medicine, 4th ed. (Cousins et al., eds.); Ch. 20; Lippincott Williams and Wilkins; pp. 464-477; (year of pub sufficiently earlier than effective US filing date and any foreign priority date) 2009.

Cleeland et al.; Pain assessment: global use of the Brief Pain Inventory; Annals, Academy of Medicine, Singapore; 23(2); pp. 129-138; Mar. 1994.

Dickinson et al.; Maldynia: pathophysiology and management of neuropathic and maladaptive pain a report of the AMA Council on Science and Public Health; Pain Medicine; 11(11); pp. 1635-1653; Nov. 1, 2010.

Dworkin et al.; Interpreting the clinical importance of treatment outcomes in chronic pain clinical trials: IMMPACT recommendations; The Journal of Pain; 9(2); pp. 105-121; Feb. 1, 2008.

Fisher et al.; Chronic stability and selectivity of four-contact spiral nerve-cuff electrodes in stimulating the human femoral nerve; J. Neural Eng.; 6(4); pp. 1-16; Aug. 2009.

Flor et al.; Phantom limb pain: a case of maladaptive CNS plasticity? Nature Reviews Neuroscience; 7(11); pp. 873-881; Nov. 2006.

Fyfe, N.; An audit of amputation levels in patients referred for prosthetic rehabilitation; Prosthetics and Orthotics International; 14(2); pp. 67-70; Aug. 1990.

Gerges et al.; Frequency- and amplitude-transitioned waveforms mitigate the onset response in high-frequency nerve block; Journal of Neural Engineering; 7(6); pp. 1-17; Dec. 2010.

Guse et al.; Outcomes of the surgical treatment of peripheral neuromas of the hand and forearm: a 25-year comparative outcome study; Annals of plastic surgery; 71(6); pp. 654-658; (abstract) Dec. 1, 2013.

(56) References Cited

OTHER PUBLICATIONS

Hadzic et al.; Neurologic complications of peripheral nerve blocks. In Peripheral nerve blocks: principles and practice, 3rd ed. (Hadzic and Vloka, eds.); Ch. 6; New York: McGraw-Hill; pp. 67-77; Sep. 20, 2004.

Haroutounian et al.; Primary afferent input critical for maintaining spontaneous pain in peripheral neuropathy; PAIN; 155(7); pp. 1272-1279 (abstract); Jul. 1, 2014.

Hsu et al.; Postamputation pain: epidemiology, mechanisms, and treatment; Journal of Pain Research; 6; pp. 121-136; Feb. 12, 2013.

Keller et al.; Validity of the brief pain inventory for use in documenting the outcomes of patients with noncancer pain; The Clinical Journal of Pain; 20(5); pp. 309-318; Sep. 1, 2004.

Kilgore et al.; Block of mammalian motor nerve conduction using high frequency alternating current; 10th Annual Conference of International FES Society; Montreal, Canada; pp. 479-481; Jul. 2005.

Kilgore et al.; Nerve conduction block utilizing high-frequency alternating current; Med. Biol. Eng. Comput.; 42(3); pp. 394-406; May 1, 2004.

Kilgore et al.; Reversible nerve conduction block using kilohertz frequency alternating current; Neuromodulation: Technology at the Neural Interface; 17(3); pp. 242-255; Apr. 2014.

Kumar et al.; Spinal cord stimulation versus conventional medical management for neuropathic pain: A multicentre randomised controlled trial in patients with failed back surgery syndrome; Pain; 132(1-2); pp. 179-188; Nov. 1, 2007.

Leland et al.; American war and military operations casualties: lists and statistics. Congressional Research Service; CRS Report to Congress; RL32492; pp. 1-30; Feb. 26, 2010.

Lewin-Kowalik et al.; Prevention and management of painful neuroma; Neurol Med Chir (Tokyo); 46(2); pp. 62-68; Feb. 2006.

Melzack et al.; Pain mechanisms: a new theory; Science; 150(3699); pp. 971-979; Nov. 19, 1965.

Miles et al.; Effects of ramped amplitude waveforms on the response of high-frequency mammalian nerve block; Journal of Neural Engineering; 4(4); pp. 390-398; Nov. 12, 2007.

Naples et al.; A spiral nerve cuff electrode for peripheral nerve stimulation; IEEE Transactions on Biomedical Engineering; 35(11); pp. 905-916; Nov. 1988.

Narang et al.; Functional capabilities of lower limb amputees; Prosthetics and Orthotics International; 8(1); pp. 43-51; Jan. 1, 1984.

NLLIC Staff. Fact Sheet. Amputation Statistics by Cause Limb Loss in the United States. Amputee Coalition of America (2008) 2 pages; retrieved from internet site http://www.amputee-coalitionsorg/fact_sheets/amp_stats_cause.pdf; Accessed Aug. 26, 2014; (year of pub sufficiently earlier than effective US filing date and any foreign priority date) 2008.

North et al.; Spinal cord stimulation versus re-operation in patients with failed back surgery syndrome: an international multicenter randomized controlled trial (EVIDENCE study); Neuromodulation: Technology at the Neural Interface; 14(4); pp. 330-336; Jul. 2011.

Page et al.; Oral Posters—Intrathecal Drug Delivery for Pain and Spasticity: 2013 1630-1640; Spine; 11-June-004. Effect of intrathecal intermittent boluses and morphine concentration on the incidence of inflammatory mass in a canine model; International Modulation Society; pp. 272-273; Jun. 11, 2013.

Pohjolainen et al.; Prosthetic use and functional and social outcome following major lower limb amputation; Prosthetics and Orthotics Intl.; 14(2); pp. 75-79; Jan. 1, 1990.

Polasek et al.; Stimulation stability and selectivity of chronically implanted multicontact nerve cuff electrodes in the human upper extremity; IEEE Transactions on Neural Systems and Rehabilitation Engineering; 17(5); pp. 428-437; Oct. 2009.

Saper et al.; Occipital nerve stimulation for the treatment of intractable chronic migraine headache: ONSTIM feasibility study; Cephalalgia; 31(3); pp. 271-285; Feb. 2011.

Schoppen et al.; Physical, mental, and social predictors of functional outcome in unilateral lower-limb amputees; Arch Phys Med Rehabil; 84(6); pp. 803-811; Jun. 1, 2003.

Sikka; Facial expression analysis for estimating pain in clinical settings; In Proceedings of the 16th International Conference on Multimodal Interaction; pp. 349-353; Nov. 2014.

Soin et al.; High-frequency electrical nerve block for post amputation pain: a pilot study; Neuromodulation; 16(5); 9 pages; Sep. 1, 2013.

Soin et al.; Feasibility study on high-frequency electrical nerve block for amputation pain; Neuromodulation; 14(6); p. 561; Nov. 1, 2011.

Subedi et al.; Phantom limb pain: mechanisms and treatment approaches; Pain Research and Treatment; Article ID 864605; 8 pages; (year of pub sufficiently earlier than effective US filing date and any foreign priority date) 2011.

Vaso et al.; Peripheral nervous system origin of phantom limb pain; PAIN; 155(7); pp. 1384-1391; Jul. 1, 2014.

Waataja et al.; Effects of high-frequency alternating current on axonal conduction through the vagus nerve; J. Neural Eng.; 8(5); pp. 1-7; Sep. 15, 2011.

Ziegler-Graham et al.; Estimating the Prevalence of Limb Loss in the United States: 2005 to 2050; Arch Phys Med Rehabil; 89(3); pp. 422-429; Mar. 1, 2008.

Fang et al.; U.S. Appl. No. 17/265,532 entitled "Apparatuses and methods for adjusting a therapeutic electrical dose," filed Feb. 3, 2021.

Syed Shah et al.; U.S. Appl. No. 17/455,392 entitled "Apparatuses and methods for setting an electrical dose," filed Nov. 17, 2021.

Snyder; U.S. Appl. No. 17/444,876 entitled "Nerve cuff deployment devices," filed Aug. 11, 2021.

* cited by examiner

SYSTEM AND METHOD FOR QUANTIFYING QUALITATIVE PATIENT-REPORTED DATA SETS

CROSS REFERENCE TO RELATED APPLICATIONS

This patent application claims priority to U.S. Provisional Patent Application No. 62/975,093, titled "METHOD FOR QUANTIFYING QUALITATIVE PATIENT-REPORTED DATA SETS," and filed on Feb. 11, 2020, which is expressly incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The inventions described herein relate to the field of neuromodulators, including (but not limited to) implantable neuromodulators.

BACKGROUND

Neuromodulators (e.g., implantable neurostimulators) are increasingly used to treat pain and other indications, in many cases by the direct application of electrical energy to one or more nerves, including nerve bundles. Such electrical modulation may be used to excite or inhibit nerves, or both. An implantable neuromodulator may be implanted on, around or adjacent to a patient's nerve or nerves for the delivery of electrical energy.

For example, electrical modulation may be applied to a nerve to treat the unwanted and/or uncoordinated generation of nerve impulses which may otherwise be a disabling factor in some medical conditions. Uncoordinated motor signals may produce spasticity in stroke, cerebral palsy, multiple sclerosis, and other conditions and may lead to pain, including pain resulting from amputation. The uncoordinated signals may result in the inability to make desired functional movements. Involuntary motor signals in conditions including tics, choreas, and so on, may produce unwanted movements. Unwanted sensory signals can cause pain.

Electrical modulation to treat a patient is generally sensitive to the amount, duration and intensity of the applied energy. For example, one non-limiting type of electrical therapy is applying high-frequency alternating current (HFAC) to nerves that has been shown to block nerve activity, e.g., in the treatment of pain. An appropriate dose (e.g., the amount of electrical energy applied to the patient for effective treatment) may be set so that it causes the desired effect, such as inhibition of nerve activity to reduce pain. On the other hand, an inappropriate dosing may lead to no effect or possibly to irritation of the nerve.

One way of determining whether an appropriate dose of energy is applied is by obtaining patient feedback. For example, in a clinical setting, the patient can be asked when and how much the pain subsides as increasing doses of energy are applied to the patient's body. When an appropriate dose is identified, the neuromodulator can be programmed to apply such dose to the patient outside of the clinical setting. Unfortunately, the optimal dosing may vary over time as the patient may experience different amounts of pain on different days, different times of a given day or when in different circumstances. Thus, it would be beneficial to provide a method and/or apparatus for reliably quantifying a patient's experience of pain outside of the clinical setting and in various circumstances, and to correlate these experiences with various dose parameters (treatment parameters) to generate a dosage regimen that effectively treats the patient's pain. Described herein are methods and apparatuses that may address these needs.

SUMMARY OF THE DISCLOSURE

Described herein are methods and apparatuses (devices, systems, etc., including neuromodulators and systems including them) for setting the therapeutic dosing of a neuromodulator, including a neuromodulator that is implanted in a patient. The neuromodulator apparatuses include a control system configured to optimize dosing based on patient-reported information. The patient reported information can be entered directly from the patient or indirectly collected by the neuromodulator apparatus based on biometric sensing. The patient-reported data can be collected in an electronic diary (eDiary), which is correlated with data from a dosage log containing a history of dosing events implemented by the neuromodulator on the patient. The correlated data can be used as feedback for generating a dosage regimen that is customized to a patient's specific needs.

The neuromodulator apparatuses described herein can include one or more controllers for controlling the energy parameters applied by one or more electrodes to the patient. The treatment dose can refer to the various energy parameters (e.g., intensity/amplitude, duration, frequency, voltage/current, and/or other treatment parameters) applied to the patient in a given treatment period. A dosage regimen can refer to the application of one or more doses to the patient over longer periods time, generally over the course of days, weeks, months or years. The dosage regimen may include a prescribed delay between applications of the individual doses.

The neuromodulators generally include an implantable waveform generator and one or more electrodes. The waveform generator includes a controller for controlling parameters of the one or more treatment doses applied by the electrode(s). The waveform generator is typically coupled to a patient controller that communicates (e.g., wirelessly) to the waveform generator and dictates the treatment doses, including any modification to the treatment doses. The patient controller can include a user interface that allows the user to choose when to apply the treatment doses. The patient controller and/or the waveform generator can also include a database log that includes a history of treatment dosages applied to the patient by the neuromodulator. The log can include a timestamp and the treatment parameters of each of the applied doses. In some cases, a separate device (e.g., smart phone, table computer, watch, laptop) is configured to allow the user to report information into the eDiary mobile application. In other examples, the patient reports eDiary information on the patient controller.

The methods and apparatuses described herein may also be configured for operation with or as an external (non-implanted) neuromodulator, including a neuromodulator that is used externally by contacting the skin of the patient.

The data collected in the eDiary can include any information useful as feedback for improving the treatment implemented by the neuromodulator. The data may include a patient-reported pain score corresponding to a level of pain experienced by the patient in real time. The pain score may be quantified using a ranking system to characterize the experience pain by severity. For example, the pain score may be ranked by severity using levels 0-10, or other conventional ranking systems. Generally, the pain score is associated with a timestamp corresponding to the time in which the patient reported the pain score. The patient is generally encouraged to report a pain score before and after applying a therapeutic treatment dose by the neuromodulator to treat the pain. The pre-treatment pain score can then be compared with the post-treatment pain score to determine a treatment outcome level of the applied treatment dose.

According to some examples, the patient-reported data in the eDiary is matched with corresponding applied treatments collected by the patient controller, based on the timestamps associated with each of the patient-reported and applied treatment data. This information can be used to determine which doses, and which treatment parameters, result in the highest treatment outcome. Further, this information can be used to determine when certain treatment doses work more effectively compared to other doses. Once these correlations are identified, one or more optimized therapeutic doses can be prescribed. Additionally, this information can be used to generate a treatment regimen that is customized for the particular patient.

The methods and apparatuses described herein may include a validation procedure to filter out data that is likely to be unrepresentative of a patient's pre and/or post treatment pain, thereby improving the reliability of the treatment outcome level and the accuracy of the optimized therapeutic dose and dosage regimen. For example, a set of validated pre-treatment pain scores can be validated by determining if a pain score timestamp of each of the pre-treatment pain scores is within a predetermined time window of a corresponding treatment initiation timestamp. Those pain scores that are outside of the time window can be excluded in the correlation analysis. In some cases, the validated pain scores are further characterized by how close a pain score was reported with respect to the corresponding treatment time. This information can be used to assess the patient's compliance and to instruct the patient how to improve use of the device.

In general, these methods may be applied to, but are not limited to, the use with neuromodulation to provide a high-frequency block of a nerve or bundle of nerves. For example, these methods and apparatuses may be used to set and/or optimize therapy treatment dosing for a high-frequency block of a nerve such as the sciatic nerve, dorsal root ganglion (DRG), etc. The one or more therapeutic doses may be beyond a nerve activation level and within a nerve blocking level of the patient.

The therapeutic dose duration of any of the methods described herein may be any appropriate length of time, e.g., between about 5 minutes and about 2 hours, e.g., between about 10 minutes and 1 hours, between about 15 minutes and 50 minutes, between about 20 minutes and 45 minutes, between about 25 minutes and about 40 minutes, etc., such as about 30 minutes. In any of the methods and apparatuses described herein the dose duration may be adjustable; for example, the duration may be set by the user, by the medical practitioner (e.g., physician, nurse, etc.) or both. In some examples the apparatus may automatically adjust the dose duration based on feedback from the system and/or patient.

In general, the applied therapeutic energy may include a high-frequency modulation signal (waveform). For example, the frequency of the applied therapeutic energy may range from about 1 kHz to about 100 kHz. In some cases, the frequency is ramped to the predetermined high frequency, where the frequency is maintained for a remainder of the treatment dose.

Any of the methods described herein may include systems that are configured to implement any of the methods described herein either automatically or semi-automatically. For example, the customized dosage regimen may be automatically implemented to provide the prescribed dosage(s) to the patient. In some cases, some or all of the customized dosage regimen can be overridden by the patient and/or a clinician.

The computer-implemented methods may include any of the steps described above, and may be implemented by one or more controllers. For example, a patient controller that communicates with a waveform generator may implement one or more of the methods. Alternatively or additionally, a controller separate from the patient controller, which communicates with the patient controller, may implement one or more of the methods.

For example, described herein are methods of treating pain in a patient using a neuromodulator, comprising: receiving a set of patient-reported pain scores including pre-treatment pain scores and post-treatment pain scores, each patient-reported pain score associated with a pain score timestamp; receiving a set of treatment dosages corresponding to treatment doses applied to the patient by the neuromodulator, each treatment dose having associated treatment parameters and a treatment initiation timestamp; establishing a set of validated pre-treatment pain scores by determining if a pain score timestamp of each of the pre-treatment pain scores is within a predetermined time window of a corresponding treatment initiation timestamp; associating a level of treatment effectiveness with each of the treatment doses applied to the patient by comparing each of the validated pre-treatment pain score with a corresponding post-treatment pain score; generating a customized dosage regimen based on the associated levels of treatment effectiveness of the treatment doses; and applying the customized dosage regimen to the patient using the neuromodulator.

The customized dosage regimen may be automatically applied to the patient using a controller of the neuromodulator. The controller may be configured to turn the neuromodulator on.

In any of these methods, a first therapeutic dose may be applied by the controller when a subsequently collected patient-reported pain score is below a threshold pain score, and a second therapeutic dose is applied by the controller when the subsequently collected patient-reported pain score is above the threshold pain score.

The one or more therapeutic doses may include a first therapeutic dose and a second therapeutic dose higher than the first therapeutic dose.

Any of these methods may include sending treatment parameters associated with the one or more therapeutic doses to the neuromodulator for applying the one or more therapeutic doses to the patient. Any of these methods may include iteratively modifying the customized dosage regimen based on the subsequently collected patient-reported pain scores.

In some examples, the methods may include assigning a confidence level to the particular patient-reported pain score, wherein the particular patient-reported pain score has: a good confidence level when within a first time prior to the particular treatment initiation timestamp, and/or a fair confidence level when within a second time prior after the particular treatment initiation timestamp. The set of validated pre-treatment pain scores may only include patient-reported pain scores assigned as having good confidence levels. In some examples, the set of validated pre-treatment pain scores may include patient-reported pain scores assigned as having good confidence levels and fair confidence levels.

The one or more therapeutic doses may be beyond a nerve activation level and within a nerve blocking level of the patient. The parameters of the therapeutic doses (which may be referred to as dose parameters or in some examples, treatment parameters) may include one or more of: amplitude, duration, frequency and voltage.

The one or more therapeutic doses may include a therapeutic dose duration including a therapy ramp-up time to reach a peak modulation voltage and a sustained peak modulation time during which the voltage is sustained at the peak modulation voltage. The set of patient-reported pain scores may be received from a portable electronic device, and wherein the set of treatment dosages is received from a patient controller.

Also described herein are systems comprising: a neuromodulator; a controller for controlling the application of a therapeutic dose by the neuromodulator, the controller including one or more processors; and memory accessible by the one or more processors, the memory storing computer-executable instructions, that, when executed by the one or more processors, implement a computer-implemented method comprising: receiving a set of patient-reported pain scores including pre-treatment pain scores and post-treatment pain scores, wherein each patient-reported pain score in the set is associated with a pain score timestamp; receiving a set of treatment dosages corresponding treatment doses applied to a patient by the neuromodulator, each treatment dose having associated treatment parameters and a treatment initiation timestamp; establishing a set of validated pre-treatment pain scores by determining if a pain score timestamp of each of the pre-treatment pain scores is within a predetermined time window of a corresponding treatment initiation timestamp; associating a level of treatment effectiveness with each of the treatment doses applied to the patient by comparing each of the validated pre-treatment pain score with a corresponding post-treatment pain score; generating a customized dosage regimen based on the associated levels of treatment effectiveness of the treatment doses; and applying the customized dosage regimen to the patient using the neuromodulator.

For example, the computer-executable instructions may be further configured to automatically apply the customized dosage regimen to the patient using the neuromodulator. These instructions may be configured by including software and/or firmware including instructions for automatically applying the customized dosage regimen by operating the controller, and in some cases a power supply coupled to a pulse generator and control circuitry.

In some examples the memory is within the neuromodulator. Alternatively, the memory (including the instructions) may be remote to the implanted neuromodulator and may wirelessly communicate with the controller of the neuromodulator. The controller may include control circuitry including wireless (e.g., Wi-Fi, Bluetooth, etc.) circuitry. The controller may be configured, e.g., by including control circuitry and/or software and/or firmware to turn the neuromodulator on and/or off (and/or to put the neuromodulator into a standby mode).

The controller may be configured to deliver a first therapeutic dose when a subsequently collected patient-reported pain score is below a threshold pain score, and to apply a second therapeutic dose when the subsequently collected patient-reported pain score is above the threshold pain score. In some examples, the controller is configured to deliver a first therapeutic dose, and a second therapeutic dose that is higher than the first therapeutic dose. The controller may adjust the therapeutic dose based on treatment parameters associated with the one or more therapeutic doses received by the neuromodulator. As mentioned, the controller may include hardware, software and/or firmware to perform any or all of these functions.

In some examples the computer-executable instructions are further configured to iteratively modify the customized dosage regimen based on the subsequently collected patient-reported pain scores. The computer-executable instructions may be further configured to assign a confidence level to the particular patient-reported pain score, wherein the particular patient-reported pain score has: a good confidence level when within a first time prior to the particular treatment initiation timestamp, and a fair confidence level when within a second time prior after the particular treatment initiation timestamp, as described herein. The computer-executable instructions may be further configured so that the set of validated pre-treatment pain scores only includes patient-reported pain scores assigned as having good confidence levels. In some examples the computer-executable instructions are further configured so that the set of validated pre-treatment pain scores includes patient-reported pain scores assigned as having good confidence levels and fair confidence levels. The computer-executable instructions may be further configured so that the customized dosage regimen includes therapeutic doses that are beyond a nerve activation level and within a nerve blocking level of the patient.

In some examples the controller is configured to modify one or more of: amplitude, duration, frequency and voltage of parameters (e.g., dose parameters or treatment parameters) delivered by the neuromodulator. For example, the controller may control the pulse generator and/or associated circuitry to adjust the does parameters. The controller may control the application of the therapeutic dose by adjusting a therapeutic dose duration including a therapy ramp-up time to reach a peak modulation voltage and a sustained peak modulation time during which the voltage is sustained at the peak modulation voltage.

Any of the systems described herein may include a patient controller including one or more controls for selecting, adjusting or selecting and adjusting a set of treatment dosages wirelessly transmitted to the controller. The patient controller may be a hand-held device that the patient may operate. The hand-held controller may include one or more patient inputs and may wirelessly and securely communicate with the neuromodulator.

This material may be related to and may be used with or incorporate the techniques and apparatuses of U.S. patent application Ser. No. 16/379,053, titled "APPARATUSES AND METHODS FOR SETTING AN ELECTRICAL DOSE," filed on Apr. 9, 2019, and U.S. patent application Ser. No. 15/510,824, titled "NERVE CUFF ELECTRODE FOR NEUROMODULATION IN LARGE HUMAN NERVE TRUNKS," filed on Sep. 12, 2014, U.S. Pat. Nos. 8,983,612, and 8,731,676.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative examples, in which the principles of the invention are utilized, and the accompanying drawings of which:

FIGS. 5A-5G show example reports including comparisons of patient-reported pain scores and treatment doses applied to a patient.

DETAILED DESCRIPTION

In general, the methods and apparatuses described herein allow quantitative analysis of a patient's pain, which can be used to apply one or more optimized therapeutic doses to the patient using a neuromodulation apparatus. These methods and apparatuses may generally be described for use with an implanted neuromodulator, but may also or alternatively be used with external neuromodulators or neuromodulators prior to implantation. Further, the examples provided herein are provided in reference to neuromodulatory inhibition by the application of high-frequency neuromodulation, however these methods and apparatuses may also be used with other neurostimulatory regimes including general neuromodulation. Examples of neuromodulator apparatuses and methods that may benefit from these methods and apparatuses may include, for example, spinal cord stimulators (SCS) and any other neuromodulation application that may be improved by the optimization between therapeutic benefit and induced sensation.

The neuromodulator systems described herein can include a means for patients to enter information related to the amount of pain that they are experiencing in real time. The patient reported data can be entered before, during and/or after a dose of neuromodulation is applied to the patient. Since patients' experience of pain are highly variable, this information is key in determining the correct dosage for providing a therapeutic effect for a particular patient. Described herein are methods of collecting and quantifying patient-reported information, which can then be used to create customized treatment doses and dosage regimens for each patient.

Figure 1:
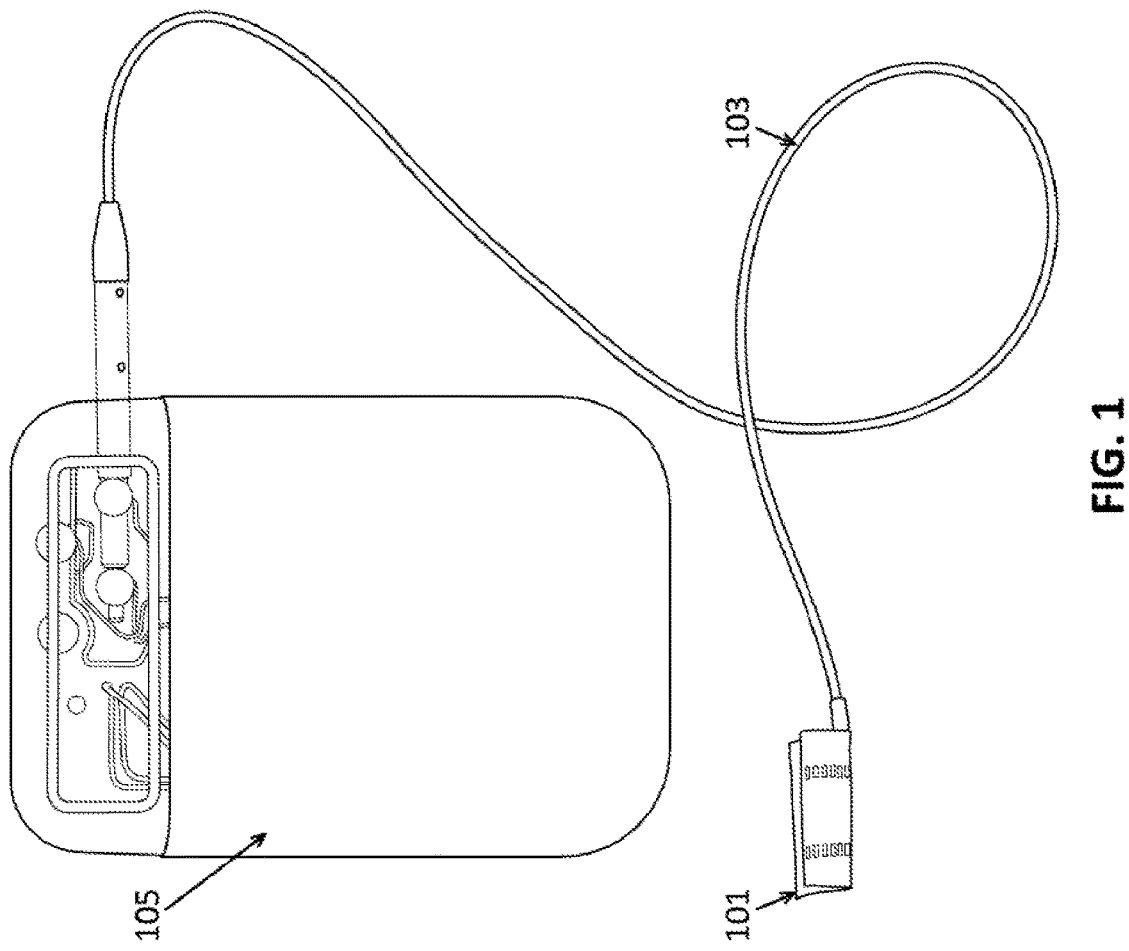
FIG. 1 shows one example of a neuromodulation system (showing a nerve cuff, lead and implantable controller/waveform generator).

The methods and apparatuses described herein may be used with any appropriate neuromodulator. FIG. 1 illustrates one example of an implantable neuromodulator including one or more electrode 101 (e.g., nerve cuff), a lead 103 connecting the electrode(s) to a waveform generator 105, which can include a controller (control circuitry), a power source, communications circuitry and/or an antenna. Systems including a nerve cuff such as those described herein, may be used, for example, to apply a high frequency nerve block to acutely treat pain, either acute pain or chronic pain (more than 6 months in duration), in humans by blocking nerve conduction of an action potential. Acute treatment may refer to on-demand treatment with substantially immediate pain relief effect. The nerve cuff may be applied onto a moderate and relatively large diameter nerves such as the sciatic nerve. One therapy involves reversibly blocking peripheral nerves by applying high frequency alternating current directly on a nerve trunk. For example, a current ranging from 1 kilohertz (kHz) to 100 kHz (e.g., 5 kHz to 50 kHz) may be applied; this may be referred to as a high frequency modulation, compared to a current of less than 1 kHz applied in the conventional electrical modulation. Efficacy of the high frequency alternating current therapy in acute non-human animal experiments (frog, cat) has been reported. U.S. Pat. Nos. 7,389,145 and 8,060,208 describe this electrical modulation technology in general.

The nerve cuffs may encircle a particular segment of a targeted peripheral nerve, e.g., a sciatic nerve, a tibial nerve, etc. Using an implanted electrode connected to an electrical waveform generator, an electrical waveform may be applied for a time interval (e.g., 10 min, 15 min, 20 min, 25 min, 30 min, 35 min, 40 min, etc.) sufficient to effect substantially immediate patient pain relief (e.g., within 10 min) and provide an extended period of pain relief (e.g., up to several hours). The current may range, for example, from 4 milliamps (mA) to 26 mA.

The application of 10 kHz alternating current generated by a custom generator via a custom implanted nerve electrode may significantly reduce pain in the majority of patients treated. For example, an implantable electrode operatively connected to an external or implanted waveform generator may be used. The electrode may be a spiral cuff electrode similar to that described in U.S. Pat. No. 4,602,624. The electrode may be implanted in a human on a desired peripheral nerve trunk proximal to the pain source (e.g., a neuroma), such that the cuff encircled the desired peripheral nerve in which the action potential was to be blocked. The cuff inner diameter may range from about 4 millimeters (mm) to about 13 mm. The sciatic nerve is known to have a relatively large nerve trunk; the diameter of the proximal part of the sciatic nerve in a human adult is about 12 mm. In one example, the apparatus and method were used on the sciatic nerve to treat limb pain in above knee amputees. In one example, the apparatus and method were used on the tibial nerve to treat limb pain in below knee amputees.

Figure 2:
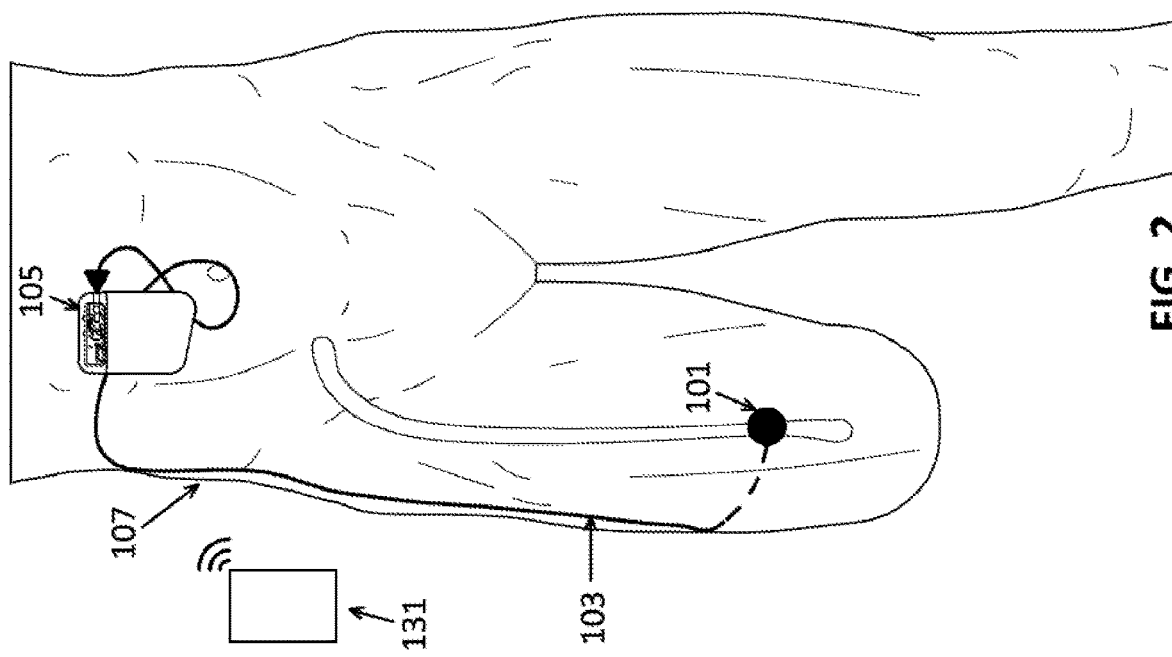
FIG. 2 shows an example of the system of FIG. 1 implanted into a patient (also showing a controller (in this example, an external controller) for controlling and applying a therapeutic dose.

For example, FIG. 2 illustrates the use of a system including a cuff electrode applied to the sciatic nerve of an amputee patient. In this example, the amputee 107 has been implanted with a nerve cuff 101 around the sciatic nerve (nerve trunk), and is connected, via a lead 103, to the controller including the waveform generator 105. This procedure may be done, for example, by first dissecting to expose the nerve in an open procedure, then wrapping the nerve with the flexible (self-closing) cuff. Once implanted the controller/waveform-generator may be placed in a pocket in the anterorlateral abdominal wall, and a tunneling electrode cable may be positioned along the midaxilalary line (including transversely across the abdomen) to connect the controller/waveform-generator to the nerve cuff electrode. Once the impedance of the nerve cuff is checked (e.g., by the controller) the incisions may be closed. The incision for implanting the nerve cuff is typically larger than about 1.5 inches (e.g., between 1.5 and 3 inches), so that sufficient visualization and access may be achieved. Once implanted and allowed to heal, the implanted neuromodulator may be set as described herein to provide an optimized therapeutic dose as described herein.

The therapeutic dose duration may be any appropriate length of time. For example, the therapeutic dose duration may range from about 5 minutes and about 2 hours (e.g., from about 10 minutes to about 1 hour, from about 15 minutes to about 50 minutes, from about 20 minutes to about 45 minutes, from about 25 minutes to about 40 minutes, or for about 30 minutes).

The neuromodulator parameters of the therapeutic dose may vary depending on, for example, the patient's specific condition and severity of symptoms. Examples of neuromodulator settings and parameters for applying therapeutic doses are described in U.S. Patent Application Publication No. 2019/0308020 A1, which is incorporated herein by reference in its entirety. The therapeutic dose can have any voltage/current profile. In some examples, a first portion of the therapeutic dose includes a ramp-up period, which has a duration between about 10% and 90% of the total duration of the therapeutic dose. A second portion of the therapeutic dose can have a sustained peak modulation time during which the voltage is sustained at the peak modulation voltage (referred to as the plateau portion). Neuromodulator may apply a high-frequency component modulation having a frequency of between about 1 kHz and 100 kHz (e.g., 1 kHz and 50 kHz, 1 kHz and 40 kHz, 1 kHz and 30 kHz, 1 kHz and 25 kHz, about 5 kHz, about 10 kHz, etc.).

The system shown in FIG. 2 also includes a patient controller 131, shown as an external device, which includes an input for the user (e.g., patient) to report a qualitative and/or quantitative experience of pain (or other sensation) before, during and/or after the applied modulation from the implanted neuromodulator, as will be described in greater detail below. The patient controller 131 may be a computing device that includes one or more processors, and may be configured to perform at least some of the methods described herein. The patient controller 131 may be a portable electronic device. In some cases, the patient controller 131 is (or is part of) a smart phone, table computer, watch, or laptop computer. The patient controller 131 may be configured to wirelessly communicate with the waveform generator 105 (e.g., while the waveform generator is implanted into the patient's body). In some cases, the waveform generator 105 and patient controller 131 are configured to communicate in a feedback loop. For example, the waveform generator can be configured to send the patient controller information regarding any treatment doses applied to the patient, and the patient controller can be configured to send the waveform generator instructions for applying the treatment doses (or modified treatment doses) based on the information from the waveform generator. In some cases, the patient controller 131 and/or the waveform generator 105 is/are configured to communicate (e.g., wired or wirelessly) to one or more additional devices.

The patient may use the patient controller 131 to enter and store information related to pain experienced outside of the clinic setting. The patient controller may include different settings for collecting information while inside the clinic (e.g., while observed or operated by a clinical specialist) and in an outpatient setting. The patient controller may be configured to collect information from the patient throughout the day in an electronic diary (eDiary). The patient controller may include a user interface, such as buttons, touch screen and/or a voice command interface, so that the patient can easily enter information. The patient may enter one or more scores that quantify a level of pain ranked by severity. Any ranking or scoring convention may be used. For instance, a pain score of level 0 (zero) may correspond to no pain, and a pain score of level 10 may correspond to the most severe pain, with pain score levels 1-9 corresponding to increasing levels of pain severity as they approach level 10. Other examples include ranking pain severity based on an alphabetical, symbolic, color and/or word system. In some instances, the pain scores are normalized using a scaling factor.

Figure 3:
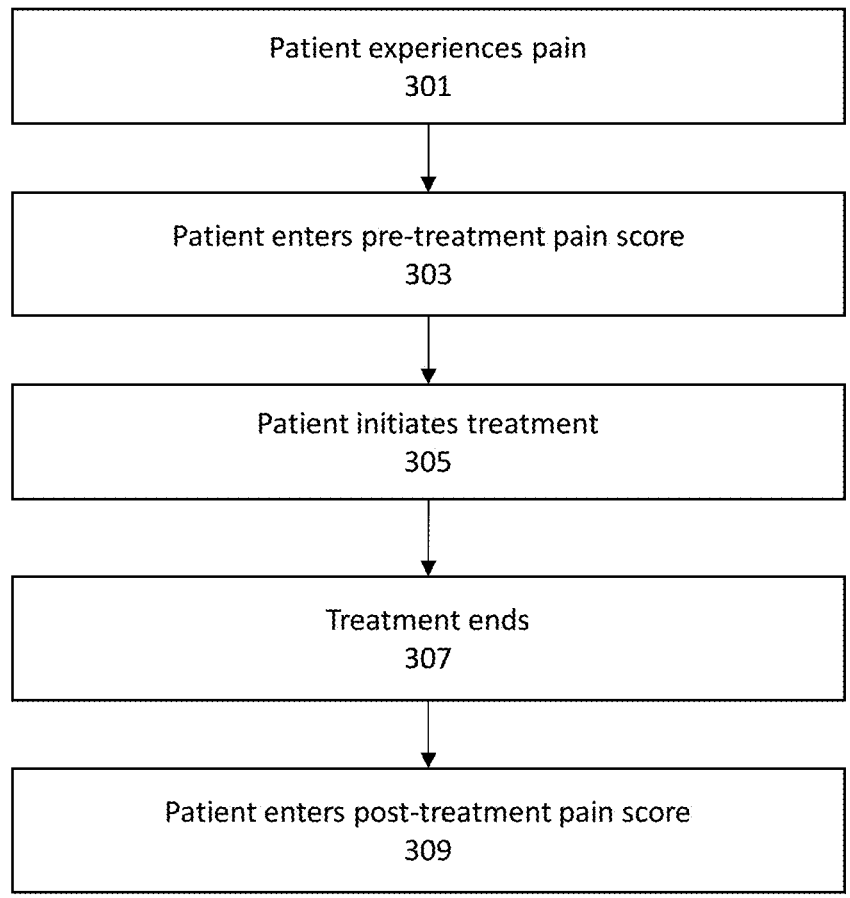
FIG. 3 is a flow diagram illustrating one method of collecting pain score data from a patient as described herein.

The patient may be encouraged to report the pain scores experienced before, during and/or after the electrode(s) apply a dose of energy. This information can be used to generate an optimal dose or dosing regimen for the patient. FIG. 3 illustrates a flowchart indicating an example process for collecting pain score data. At 301, the patient experiences pain sometime during the day. At 303, the patient enters a pre-treatment pain score using the patient controller. The pain score quantifies the level of pain experienced by the patient in real time. At 305, the patient initiates a treatment dose, at which time the implanted neuromodulator applies a preset therapeutic dose via the waveform generator and the electrode(s). In some cases, the patient chooses the treatment dose (e.g., Dose 1, Dose 2, or Dose 3, etc.). Each dose may vary depending on intensity/amplitude, duration, frequency, voltage/current, and/or other treatment parameters. At 307, the treatment dose ends after a predetermined duration of the treatment dose. At 309, the patient enters a post-treatment pain score after the treatment is complete (or near the end of treatment). In alternative examples, the patient is instructed to enter the post-treatment pain score at a time in which the patient experiences relief from the pain.

In some cases, the patient controller is configured to interrogate the patient by prompting the patient at preset times, or predetermined intervals of time. For example, the patient controller may be configured to generate an alarm (e.g., audible, visual and/or tactile alarm) to remind the patient to report an experienced level of pain. Alternatively, in some examples the apparatus may interrogate the patient indirectly, by monitoring patient biometric information (heart rate, pulse, blood pressure, ensemble nerve activity, skin conductance, respiration, biomarker, including pain biomarker, levels, etc.). In these cases, the pain score may be based on the intensity (e.g., severity) of the biometric information.

The patient's pain scores can be used to determine the effectiveness of each of the applied treatment doses, also referred to as a treatment outcome level. In some examples, the treatment outcome level is calculated by subtracting the post-treatment pain score from the pre-treatment pain score. For instance, a patient may report a pre-treatment pain score of 6 and a post-treatment pain score of 4, resulting in a treatment outcome level of 2. As another example, a patient may report a pre-treatment pain score of 6 and a post-treatment pain score of 8, resulting in a treatment outcome level of −2. In some cases, the treatment outcome levels are ranked by effectiveness: e.g., highly effective (e.g., 5 and above), moderately effective (e.g., 2 to 4), slightly effective (e.g., 1 to 2), ineffective (e.g., zero), slightly detrimental (e.g., −1 to −2 and below), moderately detrimental (e.g., −3 to −4), and highly detrimental (e.g., −5 and below). These treatment outcome levels are presented as non-limiting examples, and any ranking convention can be used.

The treatment outcome levels may be stored on the patient controller as part of the eDiary. Alternatively or additionally, the treatment outcome levels along with other data from the eDiary may be sent (e.g., wirelessly) to another device. In some cases, the eDiary data, including the treatment outcome levels, is monitored in real time, for example, by a clinical specialist. In one example, a clinical specialist downloads the eDiary data to a device separate from the patient controller.

The data collected in the eDiary, including the treatment outcome levels, can further be used to improve the treatment dosing for subsequent treatments. For example, the patient controller (or a separate device) can be used to analyze the data to find correlations between the applied dosages (including applied duration) and the treatment outcome levels. By way of example, a first treatment dose may be found to be highly effective when the patient's pre-treatment pain score is very high, but found to be only slightly effective when the patient's pre-treatment pain score is relatively low. As another example, a second treatment dose may be found to be a highly effective when applied in the morning hours of the day but found to be moderately effective when applied in the evening hours. As a further example, a high treatment dose may be found to be effective when the patient's pre-treatment pain score is very high, but found to be slightly detrimental when the patient's pre-treatment pain score is low. Thus, these correlations can elucidate links between the treatment dosage and various factors experienced by the patient that cannot be discovered in a clinical setting. Once such correlations are found, the treatment doses can be modified based on these findings so that subsequent treatments are automatically tailored to effectively treat the pain specifically experienced by the patient.

One problem encountered in the correlation analysis is that the accuracy can be highly dependent upon the timing in which the patient reports the pain scores. For example, the patient may forget to enter a pre-treatment pain score prior to or soon after applying a treatment, or forget to enter a post-treatment pain score sufficiently close to the time in which the treatment ends. This will result in under reporting of pain scores. In some cases, the patient may enter pain scores at times that are not close to any applied treatments. This will result in over reporting of pain scores. The devices and methods described herein can automatically vet the patient-reported data to determine which of the patient-reported data should be relied on for optimizing subsequent dosing regimens.

Figure 4:
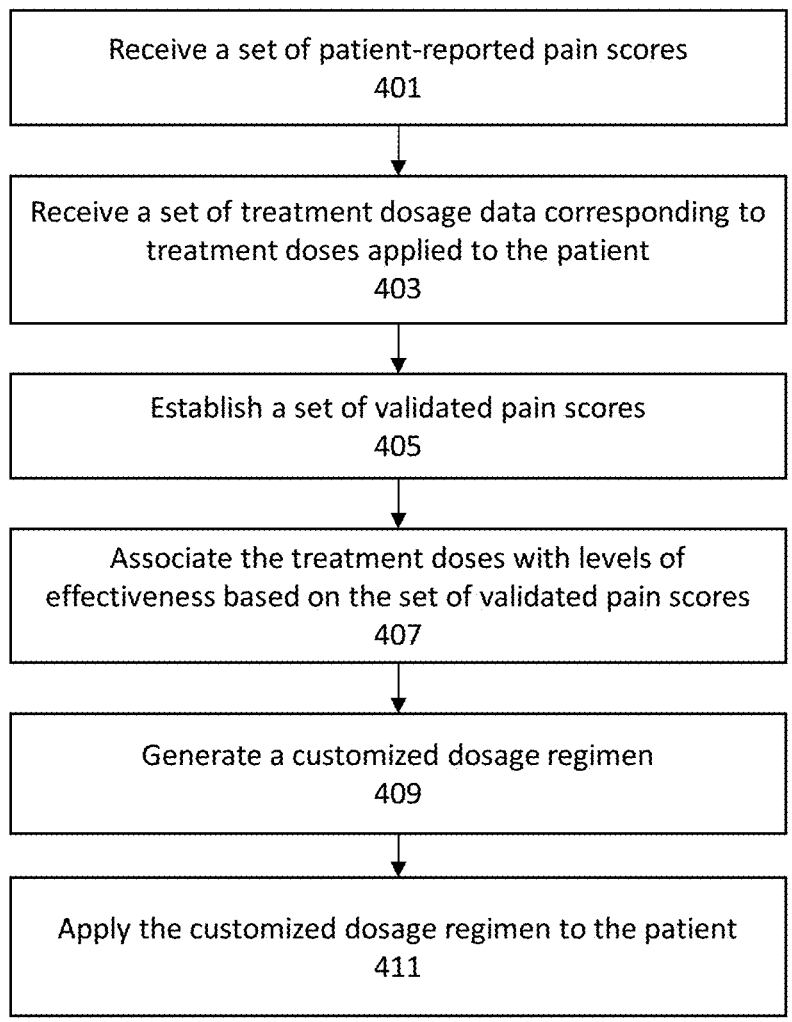
FIG. 4 is a flow diagram illustrating one method of determining a treatment dosage regimen for an implantable neuromodulator as described herein.

FIG. 4 shows a flowchart for an example process of determining a treatment dosage regimen, some or all of which can be performed by the patient controller and/or another computing device. At 401, a set of patient-reported pain scores is received. Each of the patient-reported pain scores is associated with a timestamp corresponding to the time in which the patient entered the pain score and/or indirectly collected by the patient controller based on patient biometric information. As described herein, the pain scores can be ranked by severity using any ranking system, such as a number system. At 403, a set of treatment dosage data corresponding to treatment doses applied to the patient by the neuromodulator is received. Each treatment dose has associated treatment parameters and an associated treatment initiation timestamp (i.e., time in which the treatment dose is initiated). The treatment dose may also include a duration of the treatment dose and/or an associated treatment end timestamp (i.e., time in which the treatment dose is ended). Dosage parameters may include the duration, voltage/current, frequency, amplitude/intensity of the dose, the time of day that the dose is administered, and/or other factors related to the treatment dose.

At 405, the patient-reported data is vetted to establish a set of validated pain scores. This can involve organizing the patient-reported pain scores and the treatment dosage data temporally, for example, in a single database (e.g., file). For example, a first file containing patient-reported pain scores including timestamps of the reported pain scores, and a second file containing treatment dosage data including timestamps of the treatments, can be uploaded onto a separate device, which are then combined into a single database organized temporally by timestamps. In some examples, the data is collected and combined in real time (e.g., as the patient is using the neuromodulator). In some cases, the data is combined at the patient controller itself. Once temporally organized, a particular patient-reported pain score can be temporally matched with a particular treatment dose applied to the patient. In some cases, the patient-reported pain scores are associated with a confidence level based on how temporally close the pain scores are to the applied dosages.

Figure 5A:
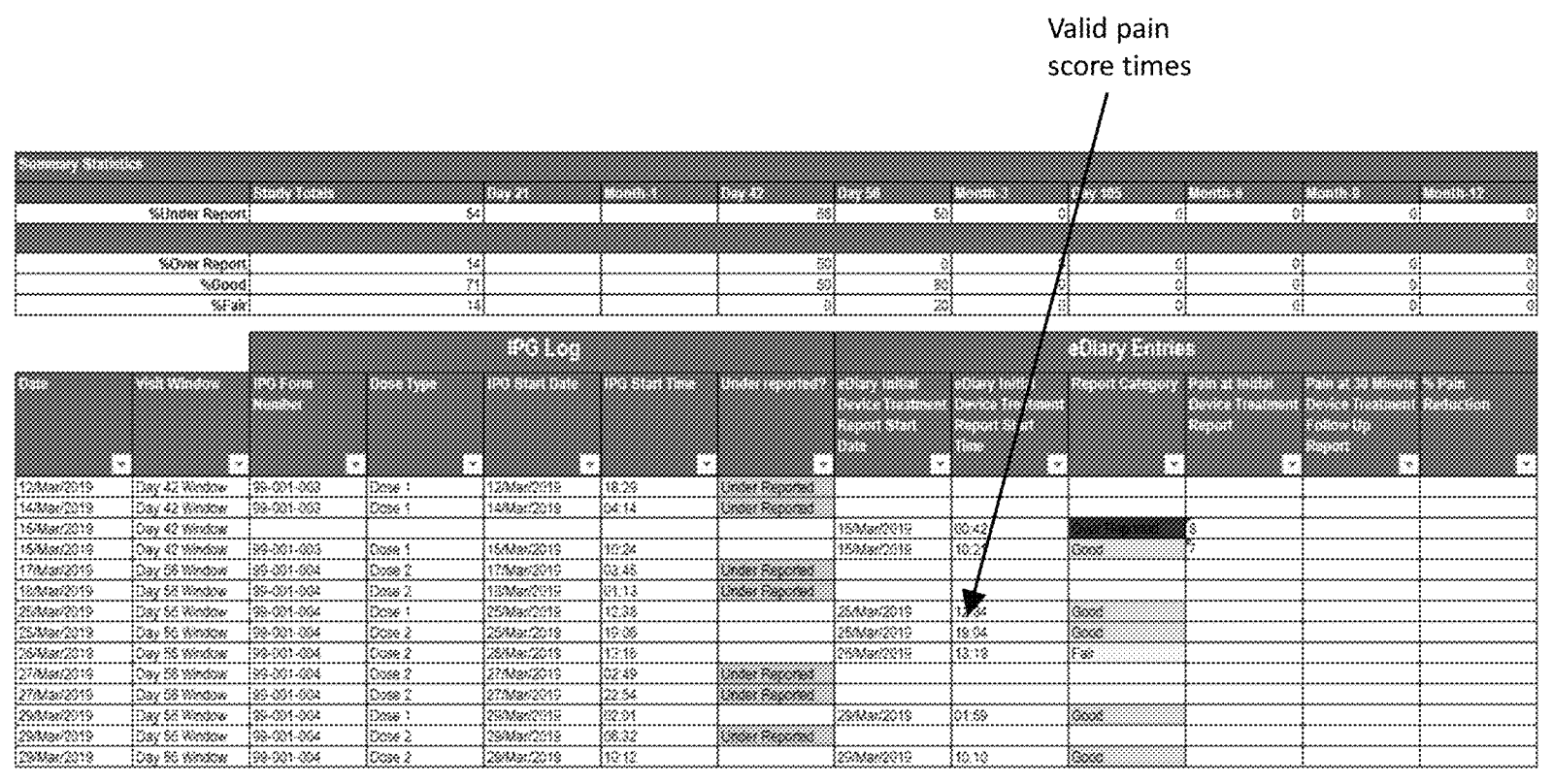
Figure 5B:
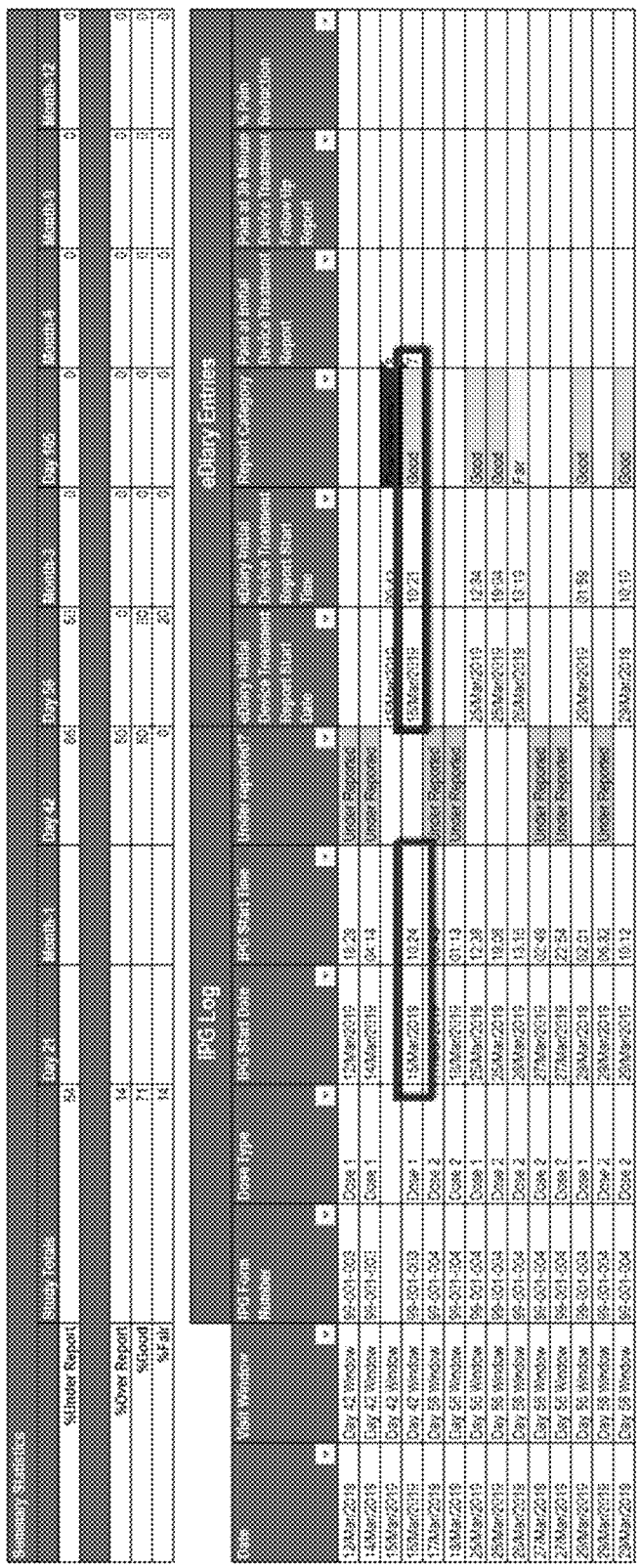
Figure 5C:
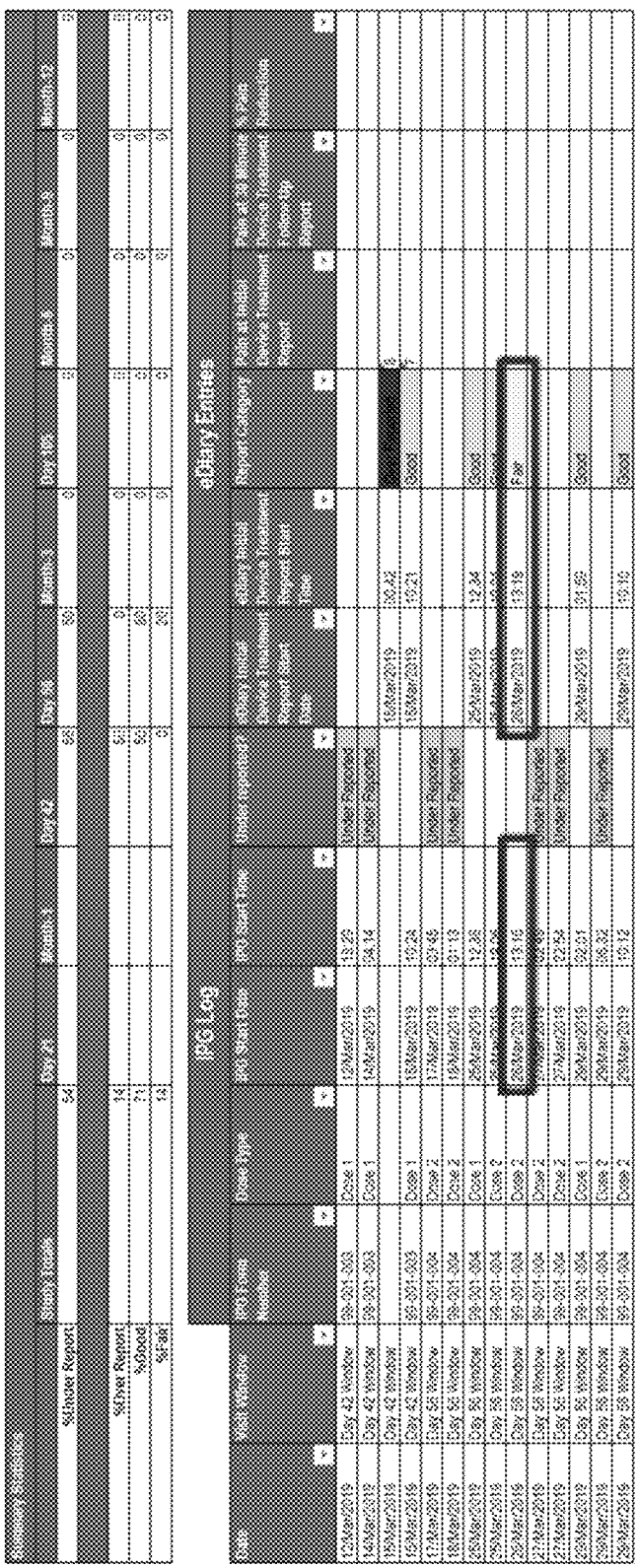
Figure 5D:
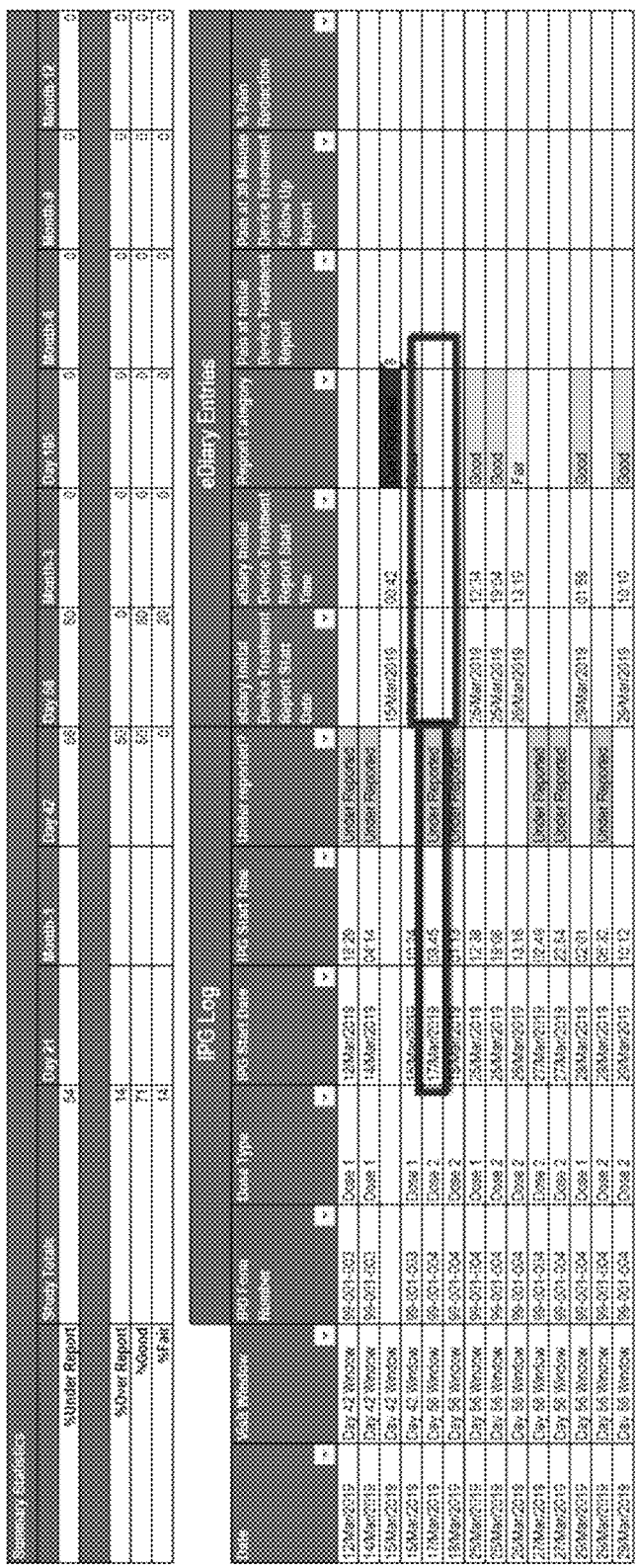
Figure 5E:
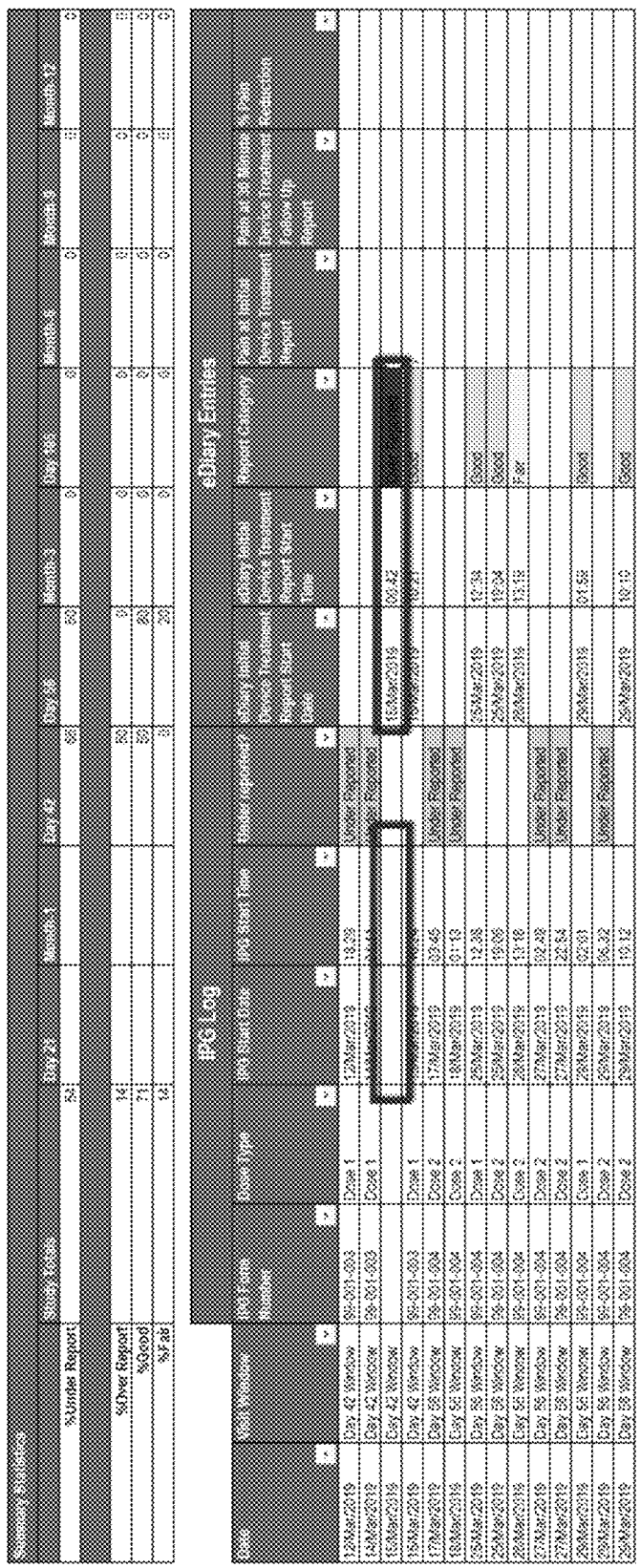

FIGS. 5A-5G illustrate example reports showing patient-reported pain scores and applied treatment doses that are temporally organized and characterized. These reports illustrate how patient-reported pain scores can be validated and assigned corresponding confidence levels. FIG. 5A illustrates an example report showing the start dates/time of applied treatment doses ("IPG Start Date" and "IPG Start Time") along with the dosage type ("Dose 1" or "Dose 2") corresponding to different treatment parameter settings of the neuromodulator when the dosages were applied to the patient. Likewise, the start dates/time of patient-reported pain score entries ("eDiary Initial Device Treatment Report Start Date" and "eDiary Initial Device Treatment Report Start Time") are also in the report. Each patient-reported entry is evaluated to determine whether the patient-reported entry is outside of a predetermined window of time relative to a corresponding treatment dose. The window of time can be within a first time prior to initiation of the treatment dose and a second time after the initiation of the treatment dose. In some examples, the first time ranges from about one to about ten minutes (e.g., 1, 2, 3, 3.5, 5, 8 or 10 minutes). In some examples, the second time ranges from about one to about ten minutes (e.g., 1, 2, 3, 3.5, 5, 8 or 10 minutes). In one particular example, the first and second times are 5 minutes. In any of the apparatuses and methods described herein, the apparatus may be configured to turn itself on. For example, the eDiary may be configured to turn the apparatus on. As mentioned, in any of these examples the eDiary may be part of and/or integrated with the patient controller.

Figure 5F:
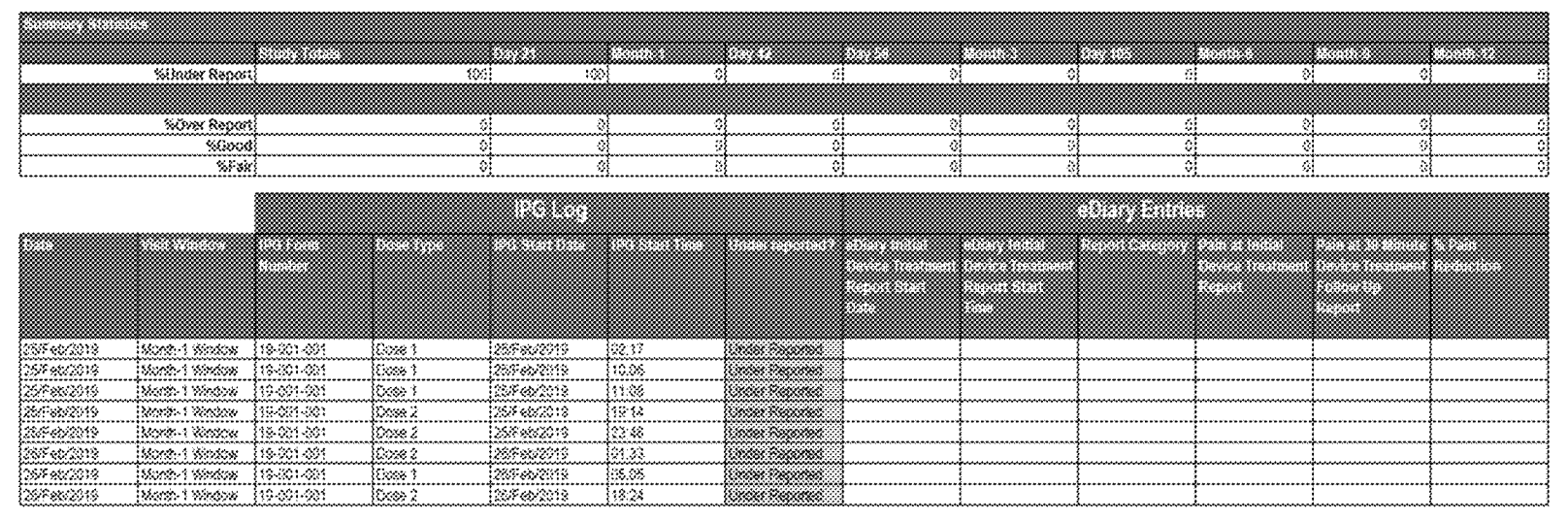
Figure 5G:
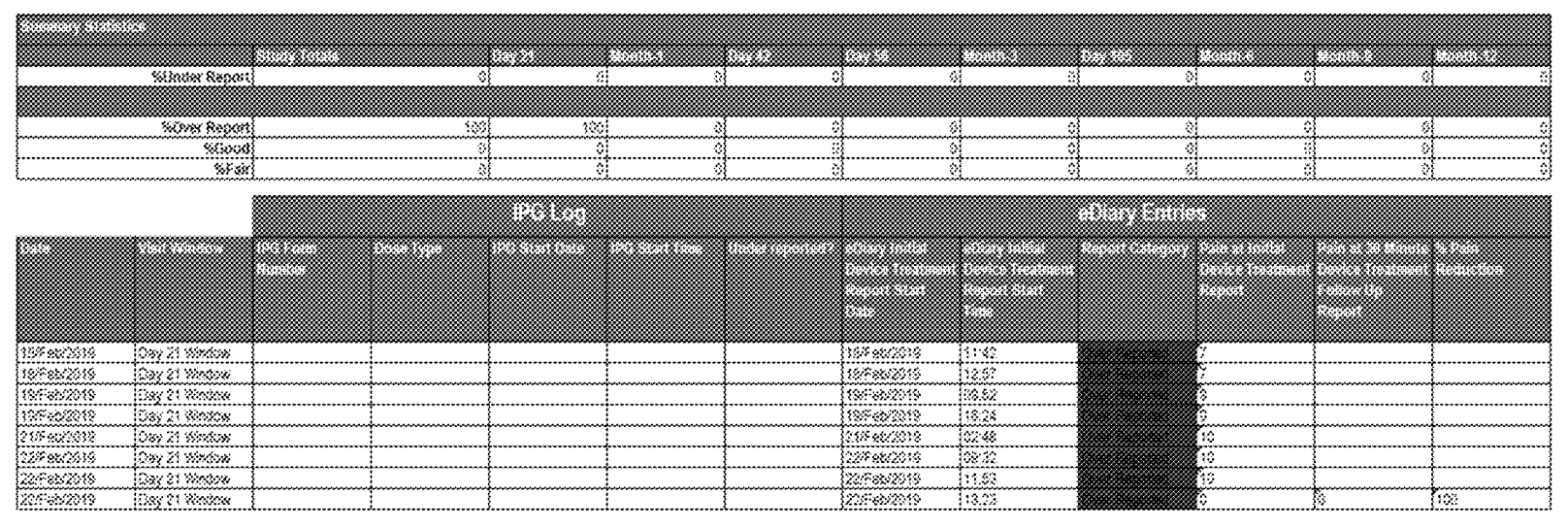

In some cases, the validated pre-treatment pain scores are further characterized by how close they are reported with respect to the corresponding dose initiation time. FIG. 5B highlights a validated pain score entry that falls within the first time prior to the initiation of the treatment dose, and is given a confidence level of "Good." FIG. 5C highlights a validated pain score entry that falls within the second time after the initiation of the treatment dose, and is given a confidence level of "Fair." FIG. 5D highlights a pain scores that falls outside of the predetermined time window (i.e., not validated), and is characterized as "Under Reported." FIG. 5E highlights an entry of a treatment dose without a corresponding pain score (i.e., not within the predetermined time window of a pain score entry), and is characterized as "Over Reported." FIG. 5F shows an example report having all "Under Reported" treatment doses, indicating that the patient did not enter any pain scores. FIG. 5G shows an example report having all "Over Reported" pain scores, indicating the patient did not initiate any treatment. In some examples, the methods described above are used, alternatively or additionally, to establish a set of validated post-treatment pain scores.

The data in the reports of FIGS. 5A-5G may be used to assess the patient's compliance and to instruct the patient how to improve compliance. For example, if the report indicates one or more "Under Reported" incidents, the patient may be instructed/reminded to report a pain score each time they treat their symptoms using the neuromodulator device. If the report indicates one or more "Over Reported" incidents, the patient may be instructed/reminded to only report a pain score when they treat their pain using the neuromodulator device. In some cases, if the report indicates one or more treatment doses characterized as having a "Fair" confidence level, the patient may be instructed/reminded to enter a pain score prior to treating their symptoms using the neuromodulator device. The instructions/reminders may be presented to the patients by the clinician, or automatically presented via a user interface (e.g., visual and/or audible alerts) of the patient controller or other device. In some cases, the instructions/reminders are presented to the patient in real time.

The report data may also be used to generate or modify a customized treatment regimen for treating the patient's pain. This can be done by determining which patient-reported pain scores should be considered as "valid" and be used in determining an optimized treatment. In one example, those patient-reported pain scores that are characterized as "Good" or "Fair" are considered valid. In another example, only those patient-reported pain scores that are characterized as "Good" are considered valid.

Returning to FIG. 4, once a set of validated pain scores (e.g., pre-treatment and/or post-treatment pain scores) is established, at 407 each of the treatment doses is associated with a level of treatment effectiveness (treatment outcome level). This can be done by comparing the validated pre-treatment pain scores with post-treatment pain scores reported by the patient. Alternatively, validated post-treatment pain scores can be compared with pre-treatment pain scores. To illustrate one non-limiting example, a validated pre-treatment pain score of 6 has a corresponding post-treatment pain score of 4, resulting in a validated treatment outcome of 2, which is associated with the treatment parameters of the Dosage 1 applied to the patient. Nominally, a number of treatment dosages are associated with corresponding validated treatment outcomes to provide results that are more reliable.

At 409, one or more customized doses are generated based on the associated levels of effectiveness (treatment outcome levels). The customized dosage regimen can be configured to optimize the treatment parameters of a given dose for achieving the highest treatment outcome level. In some cases, the optimized dose is determined based on the pre-treatment pain score. For example, if Dose 1 (e.g., higher dose) is found to provide a better treatment outcome than Dose 2 (e.g., lower dose) when the patient reports a pre-treatment pain score of 6 or above, the customized dosage regimen can prescribe Dose 1 when the patient subsequently reports a pre-treatment pain score at or above 6 or above. Thus, a first therapeutic dose can be applied when a subsequently collected patient-reported pain score is below a threshold pain score, and a second therapeutic dose can be applied when the subsequently collected patient-reported pain score is above the threshold pain score.

As another example, if Dose 1 is found to provide a better treatment outcome than Dose 2 in the evening, and Dose 2 is found to provide a better treatment outcome than Dose 1 in the morning, the dosage regimen can prescribe the best dose based on the time of day that the patient is in need of treatment. Thus, a first therapeutic dose can be applied when a subsequently collected patient-reported pain score is reported within a first time window, and a second therapeutic dose can be applied when the subsequently collected patient-reported pain score is reported within a second time window different from the first time window.

The dosage regimen may consider a combination of factors, such as dosage parameters (e.g., voltage/current, frequency, waveform, duration, and/or ramp up times), time of day (e.g. morning, afternoon, or evening), and/or biometric parameters (e.g., body temperature, and/or heart rate).

At 411, one or more doses is applied to the patient in accordance with the customized dosage regimen. The regimen may dictate which doses to apply to the patient based on subsequently collected patient-reported pain scores, the time of day, biometric parameters and/or other factors determined to affect the treatment outcome. In some cases, one or more treatment doses is applied to the patient automatically in response to the patient reporting a pre-treatment pain score above a prescribed level. In other cases, the one or more treatment doses is applied only when requested by the patient. In some examples, the one or more treatment doses is applied automatically at predetermined times independent of patient input.

In some examples, the controller is adapted to modify the customized dosage regimen iteratively using a learning algorithm (e.g., AI algorithm), making the neuromodulator device a "smart" device. For instance, the customized dosage regimen may be improved each time a validated treatment outcome is associated with corresponding parameters (dose or treatment parameters) in a feedback loop fashion (e.g., in real time). Implementation of such stimulus-response optimization algorithm can make the neuromodulator devices and therapies more adaptable based on the particular patient.

Figure 6:
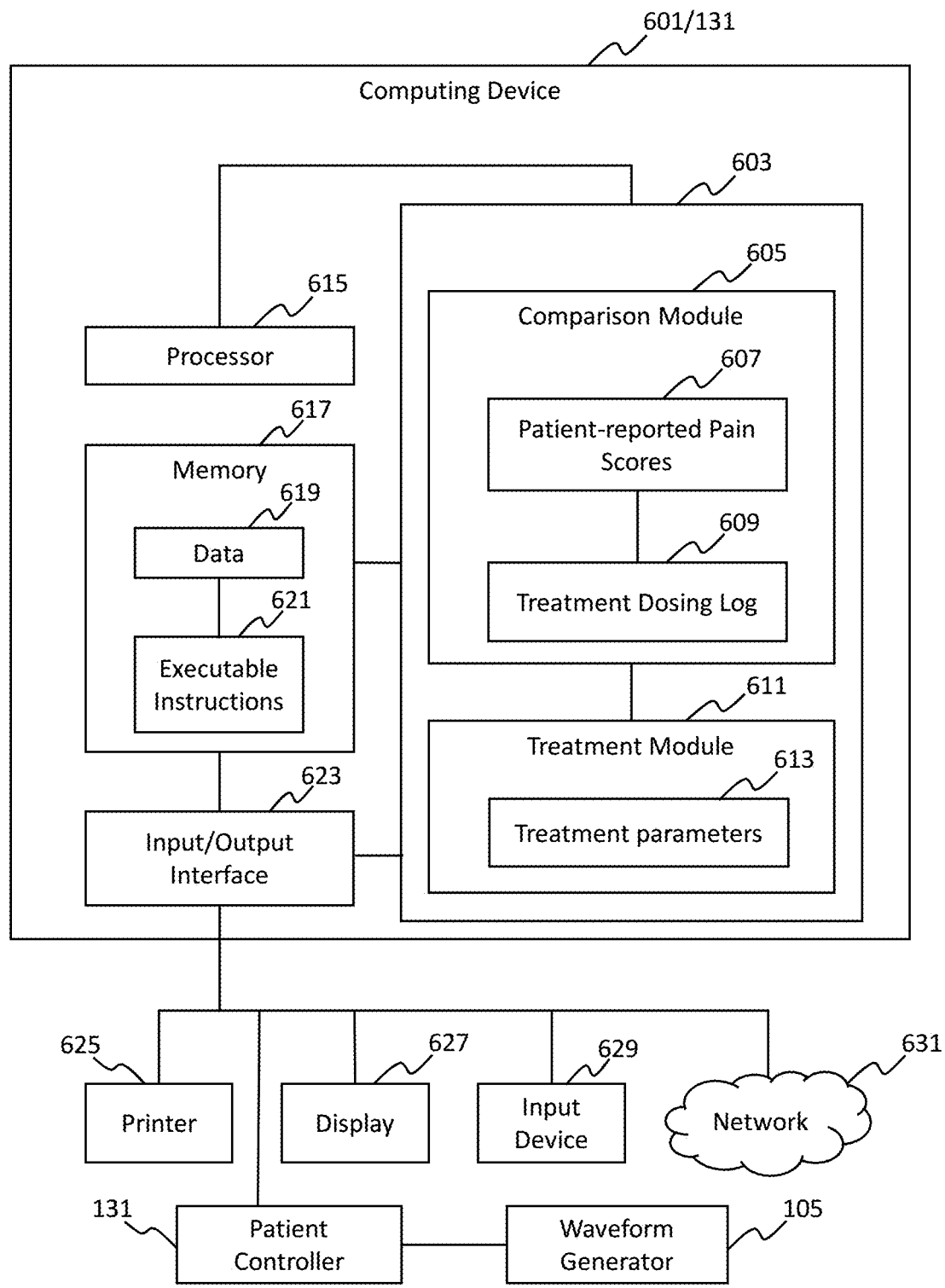
FIG. 6 illustrates a system for implementing one or more of neuromodulation methods described herein.

FIG. 6 shows a system for implementing one or more of the methods described herein. The system includes a computing device 601 having a number of components operationally coupled thereto. In some cases, the computing device 601 is a patient controller 131, as described herein. In other examples, the computing device is a device configured to communicate with the patient controller 131. In some instances, the computing device is a portable device (e.g., smart phone, table computer, watch, or laptop computer). The computing device 601 includes one or more processors 615 and memory 617. The memory can include various types of information including data 619 and executable instructions 621 as discussed herein. For example, the memory can include patient-reported pain scores, dosage parameters, dosage regimen, and associated data.

The memory and/or the processor may be located on the computing device 601 or off the device in some examples. As such, as illustrated in the example of FIG. 6, a system can include an input and/or output interface 623 configured to couple to a network 631 (e.g., local network and/or internet). Such an interface can allow for processing on another networked computing device or such devices can be used to obtain information or executable instructions for use with various examples provided herein. The input and/or output interface(s) 623. Such interfaces can also be used to connect the computing device with one or more input or output devices, such as a printer 625, a display 627 (e.g., monitor or screen), an input device 629 (e.g., mouse, keyboard, or touchscreen, etc.). If the computing device is not the patient controller 131, the input and/or output interface(s) 623 may be configured to couple with the patient controller 131, which is coupled to the waveform generator 105, as described herein. The input/output interface 623 can receive data, e.g., from the patient controller, storable in the data storage device (e.g., memory 617).

The processor(s) 615, in association with the memory 617, can be associated with data and/or one or more application modules 603. The application module(s) includes a correlation module (comparison module) 605 for correlating the patient-reported pain scores and the treatment dosing data based on time, as described herein. The comparison module may receive, store and/or process patient-reported pain scores 607 and may include treatment dosing log 609 (e.g., for storing treatment parameters and/or pain scores). A treatment module 611 is configured to generate one or more treatment doses and/or treatment dosage regimens based on results generated by the correlation module, and which can be used by the patient controller 131 to control operation of the waveform generator to apply the treatment doses and/or treatment dosage regimens on the patient. The treatment module may store and/or process treatment parameters 613.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control/perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

What is claimed is:

1. A system comprising:
   a neuromodulator;
   a controller for controlling application of a therapeutic dose by the neuromodulator, the controller including one or more processors; and
   memory accessible by the one or more processors, the memory storing computer-executable instructions, that, when executed by the one or more processors, implement a computer-implemented method comprising:
      receiving a set of patient-reported pain scores including pre-treatment pain scores and post-treatment pain scores, wherein each patient-reported pain score in the set is associated with a pain score timestamp;
      receiving a set of treatment dosages corresponding treatment doses applied to a patient by the neuromodulator, each treatment dose of the set of treatment dosages having associated treatment parameters and a treatment initiation timestamp;
      establishing a set of validated pre-treatment pain scores by determining if a pain score timestamp of each of the pre-treatment pain scores is within a predetermined time window of a corresponding treatment initiation timestamp wherein the predetermined time window is within a first time period prior to the corresponding treatment initiation timestamp and within a second time period after the corresponding treatment initiation timestamp;
      associating a level of treatment effectiveness with each of the treatment doses applied to the patient by comparing each of the validated pre-treatment pain scores with a corresponding post-treatment pain score;
      generating a customized dosage regimen based on the associated levels of treatment effectiveness of the treatment doses; and
      applying the customized dosage regimen to the patient using the neuromodulator.

2. The system of claim 1, wherein the computer-executable instructions are further configured to automatically apply the customized dosage regimen to the patient using the neuromodulator.

3. The system of claim 1, wherein the memory is within the neuromodulator.

4. The system of claim 1, wherein the controller is configured to turn the neuromodulator on.

5. The system of claim 1, wherein the controller is configured to deliver a first therapeutic dose when a subsequently collected patient-reported pain score is below a threshold pain score, and to apply a second therapeutic dose when the subsequently collected patient-reported pain score is above the threshold pain score.

6. The system of claim 1, wherein the controller is configured to deliver a first therapeutic dose, and a second therapeutic dose that is higher than the first therapeutic dose.

7. The system of claim 1, wherein the controller is configured to adjust the therapeutic dose based on treatment parameters associated with set of treatment dosages received by the neuromodulator.

8. The system of claim 1, wherein the computer-executable instructions are further configured to iteratively modify the customized dosage regimen based on subsequently collected patient-reported pain scores.

9. The system of claim 1, wherein the computer-executable instructions are further configured to assign a confidence level to a particular patient-reported pain score, wherein the particular patient-reported pain score has: a good confidence level when within a first time prior to a corresponding particular treatment initiation timestamp, and a fair confidence level when within a second time prior after the corresponding particular treatment initiation timestamp.

10. The system of claim 9, wherein the computer-executable instructions are further configured so that the set of validated pre-treatment pain scores only includes patient-reported pain scores assigned as having good confidence levels.

11. The system of claim 9, wherein the computer-executable instructions are further configured so that the set of validated pre-treatment pain scores includes patient-reported pain scores assigned as having good confidence levels and fair confidence levels.

12. The system of claim 1, wherein the computer-executable instructions are further configured so that the customized dosage regimen includes therapeutic doses that are beyond a nerve activation level and within a nerve blocking level of the patient.

13. The system of claim 1, wherein the controller is configured to modify one or more of: amplitude, duration, frequency and voltage of treatment parameters delivered by the neuromodulator.

14. The system of claim 1, wherein the controller controls the application of the therapeutic dose by adjusting a therapeutic dose duration including a therapy ramp-up time to reach a peak modulation voltage and a sustained peak modulation time during which an applied voltage is sustained at the peak modulation voltage.

15. The system of claim 1, further comprising a patient controller including one or more controls for selecting, adjusting or selecting and adjusting a set of treatment dosages wirelessly transmitted to the controller.

16. The system of claim 1, wherein each treatment dose ends after a predetermined duration, and wherein a pain score timestamp of the corresponding post-treatment pain score is after a corresponding treatment dose ends.

17. The system of claim 1, wherein each treatment dose ends after a predetermined duration, and wherein each treatment dose has an associated treatment end timestamp.

18. A method of treating pain in a patient using a neuromodulator, the method comprising:
receiving a set of patient-reported pain scores including pre-treatment pain scores and post-treatment pain scores, each patient-reported pain score associated with a pain score timestamp;
receiving a set of treatment dosages corresponding to treatment doses applied to the patient by the neuromodulator, each treatment dose of the set of treatment dosages having associated treatment parameters and a treatment initiation timestamp;
establishing a set of validated pre-treatment pain scores by determining if a pain score timestamp of each of the pre-treatment pain scores is within a predetermined time window of a corresponding treatment initiation timestamp, wherein the predetermined time window is within a first time period prior to the corresponding treatment initiation timestamp and within a second time period after the corresponding treatment initiation timestamp;
associating a level of treatment effectiveness with each of the treatment doses applied to the patient by comparing each of the validated pre-treatment pain scores with a corresponding post-treatment pain score;
generating a customized dosage regimen based on the associated levels of treatment effectiveness of the treatment doses; and
applying the customized dosage regimen to the patient using the neuromodulator.

19. The method of claim 18, wherein the customized dosage regimen is automatically applied to the patient using a controller of the neuromodulator.

20. The method of claim 19, wherein the controller is configured to turn the neuromodulator on.

21. The method of claim 19, wherein a first treatment dose is applied by the controller when a subsequently collected patient-reported pain score is below a threshold pain score, and a second treatment dose is applied by the controller when the subsequently collected patient-reported pain score is above the threshold pain score.

22. The method of claim 18, wherein the set of treatment dosages includes a first treatment dose and a second treatment dose higher than the first treatment dose.

23. The method of claim 18, further comprising sending treatment parameters associated with the set of treatment doses to the neuromodulator for applying the set of treatment dosages to the patient.

24. The method of claim 18, further comprising iteratively modifying the customized dosage regimen based on subsequently collected patient-reported pain scores.

25. The method of claim 18, further comprising assigning a confidence level to a particular patient-reported pain score, wherein the particular patient-reported pain score has:
a good confidence level when within a first time prior to a corresponding particular treatment initiation timestamp, and
a fair confidence level when within a second time prior after the corresponding particular treatment initiation timestamp.

26. The method of claim 25, wherein the set of validated pre-treatment pain scores only includes patient-reported pain scores assigned as having good confidence levels.

27. The method of claim 25, wherein the set of validated pre-treatment pain scores includes patient-reported pain scores assigned as having good confidence levels and fair confidence levels.

28. The method of claim 18, wherein the set of treatment dosages is beyond a nerve activation level and within a nerve blocking level of the patient.

29. The method of claim 18, wherein the treatment parameters include one or more of: amplitude, duration, frequency and voltage.

30. The method of claim 18, wherein the set of treatment dosages comprises a therapeutic dose duration including a therapy ramp-up time to reach a peak modulation voltage and a sustained peak modulation time during which an applied voltage is sustained at the peak modulation voltage.

31. The method of claim 18, wherein the set of patient-reported pain scores is received from a portable electronic device, and wherein the set of treatment dosages is received from a patient controller.

\* \* \* \* \*